US005795861A

United States Patent [19]

Kolterman et al.

[11] Patent Number: 5,795,861
[45] Date of Patent: Aug. 18, 1998

[54] METHODS FOR REGULATING GASTROINTESTINAL MOTILITY

[75] Inventors: Orville G. Kolterman, Poway; Timothy J. Rink, La Jolla, both of Calif.

[73] Assignee: Amylin Pharmaceuticals Inc., San Diego, Calif.

[21] Appl. No.: 471,675

[22] Filed: Jun. 5, 1995

Related U.S. Application Data

[60] Division of Ser. No. 302,069, Sep. 7, 1994, which is a continuation-in-part of Ser. No. 118,381, Sep. 7, 1993.

[51] Int. Cl.[6] .................. A61K 38/00; A61K 38/23; C04K 5/00; C04K 7/00
[52] U.S. Cl. .................. 514/12; 514/11; 514/13; 514/866; 530/307; 530/327
[58] Field of Search .................. 514/12, 11, 13, 514/866; 530/304, 324

[56] References Cited

U.S. PATENT DOCUMENTS

| | | |
|---|---|---|
| 5,124,314 | 6/1992 | Cooper .................. 514/4 |
| 5,175,145 | 12/1992 | Cooper .................. 514/4 |
| 5,187,154 | 2/1993 | Phillips et al. .................. 514/12 |
| 5,260,275 | 11/1993 | Cooper et al. .................. 514/12 |
| 5,264,372 | 11/1993 | Beaumont et al. .................. 436/504 |
| 5,266,561 | 11/1993 | Cooper et al. .................. 514/12 |
| 5,281,581 | 1/1994 | Cooper et al. .................. 514/12 |
| 5,367,052 | 11/1994 | Cooper et al. .................. 530/307 |
| 5,376,638 | 12/1994 | Young et al. .................. 514/12 |
| 5,580,953 | 12/1996 | Albrecht et al. .................. 530/303 |

FOREIGN PATENT DOCUMENTS 0 289 287 A2  2/1988  European Pat. Off.

OTHER PUBLICATIONS

Victor Plourde, Serge St. Pierre, Alan Fournier, Yvette Tache; CGRP8-27 Blocks the Inhibition of Gastric Emptying Induced by Intravenous Injection of a CGRP in Rats; Life Sciences, vol. 52 pp. 857–862 (Feb. 12, 1993).

Nagai et al., A Case of Diabetic Neuropathy Accompanied by Relapsing Paralytic Ileus Due to Omeprazole Administration; Journal of the Japan Diabetes Society 36(9)1993 Abstract.

Stacher et al., Desophageal and Gastric Motility Disorders in Patients Categorized as Having Primary Anorexia Nervosa; Gut (1986 Oct.) 27(10) Abstract.

McCallum et al., Definition of a Gastric Emptying Abnormality in Patients w/Anorexia Nervosa; Digestive Diseases and Sciences (1985 Aug.) 70(8) Abstract.

U.S. patent application Ser. No. 08/447,849, filed May 23, 1995, which is a file wrapper continuation of U.S. patent application Ser. No. 07/794,266, filed on Nov. 19, 1991, which is a continuation–in–part of U.S. patent application Ser. No. 07/667,040 filed on Mar. 8, 1991.

Alam et al., *Biochem Biophys. Res. Commun.*, 179(1):134–139 (1991).
Amara et al., *Science*, 229:1094–1097 (1985).
Brain et al., *Eur. J. Pharmacol.*, 183:2221 (1990).
Brener. et al. *Gastroenterology* 85:76–82 (1983).
Briner, *Schweiz Rundsh Med Prax* 68:1666–1672 (1979).
Broderick et al., *Biochem. Biophys. Res. Comm.*, vol. 177:932–938 (1991).
Camilleri & Malagelada, *Eur. J. Clin. Invest.* 14:420–427 (1984).
Campbell et al., *Gut* 18:462–467 (1977).
Cavallo–Perin et al., *Riv. Eur. Sci. Med. Farmacol.* 13:205–209 (1991).
Chance et al., *Brain Res.*, 539, 352–354 (1991).
Chantry et al., *Biochem. J.*, 277:139–143 (1991).
Clouse and Lustman, *Am. J. Gastoenterol.* 84:868–872 (1989).
Cooper et al., *Proc. Natl Acad. Sci.*, USA, 84:8628–8632 (1987).
Cooper et al., *Proc. Natl. Acad. Sci.*, 85:7763–7766 (1988).
Cooper et al., *Biochem. Biophys. Acta*, 1014:247–258 (1989).
Cooper et al., *Prog. Growth Factor Research* 1:99–105 (1989).
Cooper et al., *Diabetes*, 497–500 (1991).
Cotroneo et al., *Diabetes Res.* 17:99–104 (1991).
Daniel et al., *Br. Med. J.*, 3:720 (1974).
Dao et al., *Gastroenterology* 98:A342 (1990).
Deems et al., *Biochem. Biophys. Res. Commun.*, 181(1):116–120 (1991).
Eisenberg et al., *Bulletin de la Societe Internatioal de Chirurgie* 3:191–198 (1972).
Feldman et al., *Gastroenterology* 77:12–17 (1979).
Feldman et al., *Ann. Int. Med.* 98:378–384 (1983).
Feldman et al., *Gastroenterology* 87:895–902 (1984).
Follett et al., *Clinical Research*, 39(1):39A (1991).
Forster and Dockray, *Neurosci. Lett.* 131:5–7 (1991).
Franken et al., *Radiology*, 146:687 (1983).
Fraser et al., *Diabetologia* 33:675–680 (1990).
Fraser et al., *Gut* 32:475–478 (1991).
Fraser et al., *Clin. Sci.* 81:281–285 (1991).
Frontoni et al., *Diabetes*, 40:568–573 (1991).
Gaber et al. *Dig. Dis.* 9:437–443 (1991).
Galeazza et al., *Peptides*, 12:585–591 (1991).
Gardiner et al., *Diabetes*, 40:948–951 (1991).
Gedulin et al., *Biochem. Biophys. Res. Commun.*, 180(1):782–789 (1991).
Gilbey et al., *J. Bone Mineral Res.*, S293 (1991).
Gill et al., *Life Sciences*, 48:703–710 (1991).
Glauser et al., *J. Am. Coll. Emergency Physns*, 8:228 (1979).
Gomez–Foix et al., *Biochem J.*, 276:607–610 (1991).

(List continued on next page.)

*Primary Examiner*—Robert J. Hill, Jr.
*Assistant Examiner*—Jennifer Harle

[57] ABSTRACT

Methods for treating conditions associated with elevated, inappropriate or undesired post-prandial blood glucose levels are disclosed which comprise administration of an effective amount of an amylin agonist alone or in conjunction with other anti-gastric emptying agents. Methods for reducing gastric motility and delaying gastric emptying for therapeutic and diagnostic purposes are also described.

6 Claims, 12 Drawing Sheets

OTHER PUBLICATIONS

Hartter et al., *Diabetologia*, 34:52–54 (1991).
Horowitz et al., *Diabetologia* 32:151–159 (1989).
Horowitz et al., *Scand J. Gastroenterol.* 26:673–684 (1991).
Horowitz et al., *Eur. J. Nucl. Med.* 18:229–234 (1991).
Horowitz et al. *Diabetologia* 36:857–862 (1993).
Horowitz et al., *Diabetologia*, 37:543–551 (1994).
Horowitz and Frazier *Diabetologia* 37:543–551 (1994).
Huang et al., *Hypertension*, 19:I-101–I-109 (1992).
Isal et al. *Gastroenterology* 88:1094 (1985).
Janssens et al. *N. Engl. J. Med.* 322:1028–1031 (1990).
Jonderko, *Gut*, 30:430–435 (1989).
Jonderko et al.., *Digestion*, 40:191–196 (1988).
Jonderko et al., *Br. J. Clin. Pharmacol.*, 24:103–105 (1987).
Kanatsuka et al., *FEBS Lett.*, 259(1), 199–201 (1989).
Katsoulis et al., *Regul. Pept.* 26:77 (1989).
Keshavarzian et al., *Am. J. Gastroent.* 82:29–35 (1987).
Koda et al., *The Lancet*, 339:1179–1180 (1992).
Koopmans et al., *Diabetologia*, 34, 218–224 (1991).
Leighton and Cooper, *Nature*, 335:632–635 (1988).
Lenz, *Am. J. Physiol. Soc'y,* G920–G924 (1988).
Lin et al. *Nippon Shokakibyo Gakkai Zasshi* 84:1–5 (1987).
Loo et al. *Gastroenterology* 86:485–494 (1984).
Lupien J.R., and Young, A.A., "Diabetes Nutrition and Metabolism—Clinical and Experimental", vol. 6(1), pp. 13–18 (Feb. 1993).
MacGregor et al. *Gastroenterology* 70:190–196 (1976).
Mecklenbeck et al. *Euro. J. Nucl. Med.* 18:FP-3H3–1 (1991).
Moberg & Carlberger, *Scand. J. Gastroent.* 9:17–21 (1973).
Molina et al., *Diabetes*, 39:260–265 (1990).
Moore and Rink, *Diabetes* 42:5,821 Jun. (1993).
Moore et al., *Biochem. Biophys. Res. Commun.*, 179(1) (1991).
Nakanome et al., *Tohoku J. Exp. Med.*, 139:205–215 (1983).
Nowak et al. *Gastroenterology* 98:A378 (1990).
Ogawa et al., *J. Clin. Invest.*, 85:973–976 (1990).
Ohsawa et al., *Biochem. Biophys. Res. Commun.*, 160(2):961–967 (1989).
Pehling et al., *J. Clin. Invest.*, 74:985–991 (1984).
Phillips et al. *N. Eng. J. Med.* 10:130–131 (1991).
Phillips et al., *J. Nucl. Med.*, 33:1496–1500 (1992).
Phillips et al. *Dig. Dis. Sci.* 38:51–58 (1993).
Plourde et al., *Life Sci.* 52:857–862 (1993).
Raybould et al., *Peptides*, 9:735–739 (1988).
Roden et al., *Diabetologia*, 35:116–120 (1992).
Saltzman and McCallum *Yale J. Biol. Med.* 56:179–187 (1983).
Sanke et al., *Diabetologia*, 34:129–132 (1991).
Scarpello et al., *Br. Med. J.* 2:671–673 (1976).
Schvarcz et al. *Diabet. Med.* 10:660–663 (1993).
Scott and Lloyd–Mostyn, *The Lancet* 1:590 (1976).
Silvestre et al., *Reg. Pept.*, 31–23–31 (1990).
Stephens, et al., *Diabetes*, 40:395–400 (1991).
Stower et al., *Br. J. Surg.*, 69:591–2 (1982).
Torsdottir et al. *J. Nutr.* 121:795–799 (1991).
Wang et al., *Biochem. Biophys. Res. Commun.*, 181(3):1288–1293 (1991).
Wang et al., *FEBS Letts.*, 219:195–198 (1991 b).
Webb et al., *Med. J. Aust.*, 144:124 (1986).
Wright and Clemente, *Gastroenterology* 84:1355 (1983).
Young et al., *Am. J. Physiol.*, 259:E457–461 (1990).
Young et al., *FEBS Letts*, 281(1,2):149–151 (1991).
Young et al., *Am.J. Physiolog.*, 263(2:E274–E281 (1992).
Young et al., *Moll. Cell. Endocrinol.*, 84:R1–R5 (1992).
Zhu et al., *Biochem. Biophys. Res. Commun.*, 177(2):771–776 (1991).
Zierath et al., *Diabetologia*, 35:26–31 (1992).
Zitomer et al., *Metabolism* 17:199–201 (1968).

SEQUENCE LISTING ( 1 ) GENERAL INFORMATION:

( i i i ) NUMBER OF SEQUENCES: 30

( 2 ) INFORMATION FOR SEQ ID NO:1:

( i ) SEQUENCE CHARACTERISTICS:
        ( A ) LENGTH: 29 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( D ) OTHER INFORMATION: amidated Phe at position 29

( x i ) SEQUENCE DESCRIPTION: SEQ ID NO:1:

Val Thr His Arg Leu Ala Gly Leu Leu Ser Arg Ser Gly Gly Val Val
1               5                   10                  15

Lys Asn Phe Val Pro Thr Asn Val Gly Ser Lys Ala Phe
            20                  25

( 2 ) INFORMATION FOR SEQ ID NO:2:

( i ) SEQUENCE CHARACTERISTICS:

( A ) LENGTH: 37 amino acids
( B ) TYPE: amino acid
( C ) STRANDEDNESS: single
( D ) TOPOLOGY: linear ( i i ) MOLECULE TYPE: peptide ( i x ) FEATURE:
( D ) OTHER INFORMATION: disulfide bridge between the Cys
residues at positions 2 and 7;
amidated Tyr at position 37

( x i ) SEQUENCE DESCRIPTION: SEQ ID NO:2:

Lys Cys Asn Thr Ala Thr Cys Ala Thr Gln Arg Leu Ala Asn Phe Leu
1               5                   10                  15
Val His Ser Ser Asn Asn Phe Gly Pro Ile Leu Pro Pro Thr Asn Val
            20                  25                  30
Gly Ser Asn Thr Tyr
            35

( 2 ) INFORMATION FOR SEQ ID NO:3:

( i ) SEQUENCE CHARACTERISTICS:
( A ) LENGTH: 24 amino acids
( B ) TYPE: amino acid
( C ) STRANDEDNESS: single
( D ) TOPOLOGY: linear ( i i ) MOLECULE TYPE: Peptide ( i x ) FEATURE:
( D ) OTHER INFORMATION: acetylated Leu at position 1;
amidated Tyr at position 24

( x i ) SEQUENCE DESCRIPTION: SEQ ID NO:3:

Leu Gly Arg Leu Ser Gln Glu Leu His Arg Leu Gln Thr Thr Pro Arg
1               5                   10                  15
Thr Asn Thr Gly Ser Asn Thr Tyr
            20

( 2 ) INFORMATION FOR SEQ ID NO:4:

( i ) SEQUENCE CHARACTERISTICS:
( A ) LENGTH: 37 amino acids
( B ) TYPE: amino acid
( C ) STRANDEDNESS: single
( D ) TOPOLOGY: linear ( i i ) MOLECULE TYPE: Peptide ( i x ) FEATURE:
( D ) OTHER INFORMATION: disulfide bridge between the Cys
residues at positions 2 and 7;
amidated Tyr at position 37

( x i ) SEQUENCE DESCRIPTION: SEQ ID NO:4:

Lys Cys Asn Thr Ala Thr Cys Ala Thr Gln Arg Leu Ala Asn Phe Leu
1               5                   10                  15
Val Arg Ser Ser Asn Asn Phe Gly Pro Ile Leu Pro Ser Thr Asn Val
            20                  25                  30
Gly Ser Asn Thr Tyr
            35

( 2 ) INFORMATION FOR SEQ ID NO:5:

( i ) SEQUENCE CHARACTERISTICS:
( A ) LENGTH: 36 amino acids
( B ) TYPE: amino acid
( C ) STRANDEDNESS: single ( D ) TOPOLOGY: linear ( i i ) MOLECULE TYPE: peptide ( i x ) FEATURE:
    ( D ) OTHER INFORMATION: disulfide bridge between the Cys
        residues at positions 1 and 6;
        amidated Tyr at position 36

( x i ) SEQUENCE DESCRIPTION: SEQ ID NO:5:

| Cys | Asn | Thr | Ala | Thr | Cys | Ala | Thr | Gln | Arg | Leu | Ala | Asn | Phe | Leu | Val |
|---|---|---|---|---|---|---|---|---|---|---|---|---|---|---|---|
| 1 | | | | 5 | | | | | 10 | | | | | 15 | |
| His | Ser | Ser | Asn | Asn | Phe | Gly | Ala | Ile | Leu | Ser | Ser | Thr | Asn | Val | Gly |
| | | | 20 | | | | | 25 | | | | 30 | | | |
| Ser | Asn | Thr | Tyr | | | | | | | | | | | | |
| | | 35 | | | | | | | | | | | | | |

( 2 ) INFORMATION FOR SEQ ID NO:6:

( i ) SEQUENCE CHARACTERISTICS:
        ( A ) LENGTH: 37 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( D ) OTHER INFORMATION: disulfide bridge between the Cys
            residues at positions 2 and 7;
            amidated Tyr at position 37

( x i ) SEQUENCE DESCRIPTION: SEQ ID NO:6:

| Lys | Cys | Asn | Thr | Ala | Thr | Cys | Ala | Thr | Gln | Arg | Leu | Ala | Asn | Phe | Leu |
|---|---|---|---|---|---|---|---|---|---|---|---|---|---|---|---|
| 1 | | | | 5 | | | | | 10 | | | | | 15 | |
| Val | His | Ser | Ser | Asn | Asn | Phe | Gly | Ala | Ile | Leu | Pro | Ser | Thr | Asn | Val |
| | | | 20 | | | | | 25 | | | | 30 | | | |
| Gly | Ser | Asn | Thr | Tyr | | | | | | | | | | | |
| | | | 35 | | | | | | | | | | | | |

( 2 ) INFORMATION FOR SEQ ID NO:7:

( i ) SEQUENCE CHARACTERISTICS:
        ( A ) LENGTH: 36 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( D ) OTHER INFORMATION: disulfide bridge between the Cys
            residues at positions 1 and 6;
            amidated Tyr at position 36

( x i ) SEQUENCE DESCRIPTION: SEQ ID NO:7:

| Cys | Asn | Thr | Ala | Thr | Cys | Ala | Thr | Gln | Arg | Leu | Ala | Asn | Phe | Leu | Val |
|---|---|---|---|---|---|---|---|---|---|---|---|---|---|---|---|
| 1 | | | | 5 | | | | | 10 | | | | | 15 | |
| Arg | Ser | Ser | Asn | Asn | Phe | Gly | Pro | Ile | Leu | Pro | Ser | Thr | Asn | Val | Gly |
| | | | 20 | | | | | 25 | | | | 30 | | | |
| Ser | Asn | Thr | Tyr | | | | | | | | | | | | |
| | | 35 | | | | | | | | | | | | | |

( 2 ) INFORMATION FOR SEQ ID NO:8:

( i ) SEQUENCE CHARACTERISTICS:
        ( A ) LENGTH: 37 amino acids
        ( B ) TYPE: amino acid ( C ) STRANDEDNESS: single
( D ) TOPOLOGY: linear ( i i ) MOLECULE TYPE: peptide ( i x ) FEATURE:
( D ) OTHER INFORMATION: disulfide bridge between the Cys
residues at positions 2 and 7;
amidated Tyr at position 37

( x i ) SEQUENCE DESCRIPTION: SEQ ID NO:8:

| Lys | Cys | Asn | Thr | Ala | Thr | Cys | Ala | Thr | Gln | Arg | Leu | Ala | Asn | Phe | Leu |
|---|---|---|---|---|---|---|---|---|---|---|---|---|---|---|---|
| 1 | | | | 5 | | | | | 10 | | | | | 15 | |

| Val | His | Ser | Ser | Asn | Asn | Phe | Gly | Pro | Val | Leu | Pro | Pro | Thr | Asn | Val |
|---|---|---|---|---|---|---|---|---|---|---|---|---|---|---|---|
| | | | 20 | | | | | 25 | | | | | 30 | | |

| Gly | Ser | Asn | Thr | Tyr |
|---|---|---|---|---|
| | | 35 | | |

( 2 ) INFORMATION FOR SEQ ID NO:9:

( i ) SEQUENCE CHARACTERISTICS:
( A ) LENGTH: 37 amino acids
( B ) TYPE: amino acid
( C ) STRANDEDNESS: single
( D ) TOPOLOGY: linear ( i i ) MOLECULE TYPE: peptide ( i x ) FEATURE:
( D ) OTHER INFORMATION: disulfide bridge between the Cys
residues at positions 2 and 7;
amidated Tyr at position 37

( x i ) SEQUENCE DESCRIPTION: SEQ ID NO:9:

| Lys | Cys | Asn | Thr | Ala | Thr | Cys | Ala | Thr | Gln | Arg | Leu | Ala | Asn | Phe | Leu |
|---|---|---|---|---|---|---|---|---|---|---|---|---|---|---|---|
| 1 | | | | 5 | | | | | 10 | | | | | 15 | |

| Val | Arg | Ser | Ser | Asn | Asn | Phe | Gly | Pro | Ile | Leu | Pro | Pro | Thr | Asn | Val |
|---|---|---|---|---|---|---|---|---|---|---|---|---|---|---|---|
| | | | 20 | | | | | 25 | | | | | 30 | | |

| Gly | Ser | Asn | Thr | Tyr |
|---|---|---|---|---|
| | | 35 | | |

( 2 ) INFORMATION FOR SEQ ID NO:10:

( i ) SEQUENCE CHARACTERISTICS:
( A ) LENGTH: 36 amino acids
( B ) TYPE: amino acid
( C ) STRANDEDNESS: single
( D ) TOPOLOGY: linear ( i i ) MOLECULE TYPE: peptide ( i x ) FEATURE:
( D ) OTHER INFORMATION: disulfide bridge between the Cys
residues at positions 1 and 6;
amidated Tyr at position 36

( x i ) SEQUENCE DESCRIPTION: SEQ ID NO:10:

| Cys | Asn | Thr | Ala | Thr | Cys | Ala | Thr | Gln | Arg | Leu | Ala | Asn | Pro | Leu | Val |
|---|---|---|---|---|---|---|---|---|---|---|---|---|---|---|---|
| 1 | | | | 5 | | | | | 10 | | | | | 15 | |

| Arg | Ser | Ser | Asn | Asn | Phe | Gly | Pro | Ile | Leu | Pro | Pro | Thr | Asn | Val | Gly |
|---|---|---|---|---|---|---|---|---|---|---|---|---|---|---|---|
| | | | 20 | | | | | 25 | | | | | 30 | | |

| Ser | Asn | Thr | Tyr |
|---|---|---|---|
| | | 35 | |

( 2 ) INFORMATION FOR SEQ ID NO:11:

( i ) SEQUENCE CHARACTERISTICS:
( A ) LENGTH: 36 amino acids (B) TYPE: amino acid
(C) STRANDEDNESS: single
(D) TOPOLOGY: linear (ii) MOLECULE TYPE: peptide (ix) FEATURE:
(D) OTHER INFORMATION: disulfide bridge between the Cys residues at positions 1 and 6; amidated Tyr at position 36

(xi) SEQUENCE DESCRIPTION: SEQ ID NO:11:

```
Cys Asn Thr Ala Thr Cys Ala Thr Gln Arg Leu Ala Asn Phe Leu Val
 1               5                  10                      15
His Ser Ser Asn Asn Phe Gly Pro Ile Leu Pro Pro Thr Asn Val Gly
            20                  25                  30
Ser Asn Thr Tyr
            35
```

(2) INFORMATION FOR SEQ ID NO:12:

(i) SEQUENCE CHARACTERISTICS:
(A) LENGTH: 37 amino acids
(B) TYPE: amino acid
(C) STRANDEDNESS: single
(D) TOPOLOGY: linear (ii) MOLECULE TYPE: peptide (ix) FEATURE:
(D) OTHER INFORMATION: disulfide bridge between the Cys residues at positions 2 and 7; amidated Tyr at position 37

(xi) SEQUENCE DESCRIPTION: SEQ ID NO:12:

```
Lys Cys Asn Thr Ala Thr Cys Ala Thr Gln Arg Leu Ala Asn Phe Leu
 1               5                  10                      15
Val His Ser Ser Asn Asn Leu Gly Pro Val Leu Pro Pro Thr Asn Val
                20                  25                  30
Gly Ser Asn Thr Tyr
            35
```

(2) INFORMATION FOR SEQ ID NO:13:

(i) SEQUENCE CHARACTERISTICS:
(A) LENGTH: 37 amino acids
(B) TYPE: amino acid
(C) STRANDEDNESS: single
(D) TOPOLOGY: linear (ii) MOLECULE TYPE: peptide (ix) FEATURE:
(D) OTHER INFORMATION: disulfide bridge between the Cys residues at positions 2 and 7; amidated Tyr at position 37

(xi) SEQUENCE DESCRIPTION: SEQ ID NO:13:

```
Lys Cys Asn Thr Ala Thr Cys Ala Thr Gln Arg Leu Ala Asn Phe Leu
 1               5                  10                      15
Val His Ser Ser Asn Asn Leu Gly Pro Val Leu Pro Ser Thr Asn Val
                20                  25                  30
Gly Ser Asn Thr Tyr
            35
```

(2) INFORMATION FOR SEQ ID NO:14:

(i) SEQUENCE CHARACTERISTICS:

(A) LENGTH: 36 amino acids
(B) TYPE: amino acid
(C) STRANDEDNESS: single
(D) TOPOLOGY: linear (ii) MOLECULE TYPE: peptide (ix) FEATURE:
(D) OTHER INFORMATION: disulfide bridge between the Cys
residues at positions 1 and 6;
amidated Tyr at position 36

(xi) SEQUENCE DESCRIPTION: SEQ ID NO:14:

Cys Asn Thr Ala Thr Cys Ala Thr Gln Arg Leu Ala Asn Phe Leu Val
1               5                   10                  15

His Ser Ser Asn Asn Leu Gly Pro Val Leu Pro Ser Thr Asn Val Gly
            20                  25                  30

Ser Asn Thr Tyr
        35

(2) INFORMATION FOR SEQ ID NO:15:

(i) SEQUENCE CHARACTERISTICS:
(A) LENGTH: 37 amino acids
(B) TYPE: amino acid
(C) STRANDEDNESS: single
(D) TOPOLOGY: linear (ii) MOLECULE TYPE: peptide (ix) FEATURE:
(D) OTHER INFORMATION: disulfide bridge between the Cys
residues at positions 2 and 7;
amidated Tyr at position 37

(xi) SEQUENCE DESCRIPTION: SEQ ID NO:15:

Lys Cys Asn Thr Ala Thr Cys Ala Thr Gln Arg Leu Ala Asn Phe Leu
1               5                   10                  15

Val Arg Ser Ser Asn Asn Leu Gly Pro Val Leu Pro Ser Thr Asn Val
            20                  25                  30

Gly Ser Asn Thr Tyr
        35

(2) INFORMATION FOR SEQ ID NO:16:

(i) SEQUENCE CHARACTERISTICS:
(A) LENGTH: 37 amino acids
(B) TYPE: amino acid
(C) STRANDEDNESS: single
(D) TOPOLOGY: linear (ii) MOLECULE TYPE: peptide (ix) FEATURE:
(D) OTHER INFORMATION: disulfide bridge between the Cys
residues at positions 2 and 7;
amidated Tyr at position 37

(xi) SEQUENCE DESCRIPTION: SEQ ID NO:16:

Lys Cys Asn Thr Ala Thr Cys Ala Thr Gln Arg Leu Ala Asn Phe Leu
1               5                   10                  15

Val Arg Ser Ser Asn Asn Leu Gly Pro Ile Leu Pro Pro Thr Asn Val
            20                  25                  30

Gly Ser Asn Thr Tyr
        35

(2) INFORMATION FOR SEQ ID NO:17:

( i ) SEQUENCE CHARACTERISTICS:
 ( A ) LENGTH: 37 amino acids
 ( B ) TYPE: amino acid
 ( C ) STRANDEDNESS: single
 ( D ) TOPOLOGY: linear ( i i ) MOLECULE TYPE: peptide ( i x ) FEATURE:
 ( D ) OTHER INFORMATION: disulfide bridge between the Cys
  residues at positions 2 and 7;
  amidated Tyr at position 37

( x i ) SEQUENCE DESCRIPTION: SEQ ID NO:17:

```
Lys Cys Asn Thr Ala Thr Cys Ala Thr Gln Arg Leu Ala Asn Phe Leu
 1               5                  10                      15

Val Arg Ser Ser Asn Asn Leu Gly Pro Ile Leu Pro Ser Thr Asn Val
            20                  25                  30

Gly Ser Asn Thr Tyr
            35
```

( 2 ) INFORMATION FOR SEQ ID NO:18:

( i ) SEQUENCE CHARACTERISTICS:
  ( A ) LENGTH: 37 amino acids
  ( B ) TYPE: amino acid
  ( C ) STRANDEDNESS: single
  ( D ) TOPOLOGY: linear ( i i ) MOLECULE TYPE: peptide ( i x ) FEATURE:
  ( D ) OTHER INFORMATION: disulfide bridge between the Cys
   residues at positions 2 and 7;
   amidated Tyr at position 37

( x i ) SEQUENCE DESCRIPTION: SEQ ID NO:18:

```
Lys Cys Asn Thr Ala Thr Cys Ala Thr Gln Arg Leu Ala Asn Phe Leu
 1               5                  10                      15

Ile His Ser Ser Asn Asn Leu Gly Pro Ile Leu Pro Pro Thr Asn Val
            20                  25                  30

Gly Ser Asn Thr Tyr
            35
```

( 2 ) INFORMATION FOR SEQ ID NO:19:

( i ) SEQUENCE CHARACTERISTICS:
  ( A ) LENGTH: 37 amino acids
  ( B ) TYPE: amino acid
  ( C ) STRANDEDNESS: single
  ( D ) TOPOLOGY: linear ( i i ) MOLECULE TYPE: peptide ( i x ) FEATURE:
  ( D ) OTHER INFORMATION: disulfide bridge between the Cys
   residues at positions 2 and 7;
   amidated Tyr at position 37

( x i ) SEQUENCE DESCRIPTION: SEQ ID NO:19:

```
Lys Cys Asn Thr Ala Thr Cys Ala Thr Gln Arg Leu Ala Asn Phe Leu
 1               5                  10                      15

Ile His Ser Ser Asn Asn Phe Gly Pro Ile Leu Pro Pro Thr Asn Val
            20                  25                  30

Gly Ser Asn Thr Tyr
            35
```

( 2 ) INFORMATION FOR SEQ ID NO:20:

( i ) SEQUENCE CHARACTERISTICS:
  ( A ) LENGTH: 36 amino acids
  ( B ) TYPE: amino acid
  ( C ) STRANDEDNESS: single
  ( D ) TOPOLOGY: linear ( i i ) MOLECULE TYPE: peptide ( i x ) FEATURE:
  ( D ) OTHER INFORMATION: disulfide bridge between the Cys residues at positions 1 and 6; amidated Tyr at position 36

( x i ) SEQUENCE DESCRIPTION: SEQ ID NO:20:

Cys Asn Thr Ala Thr Cys Ala Thr Gln Arg Leu Ala Asn Phe Leu Ile
1               5                   10                  15
His Ser Ser Asn Asn Leu Gly Pro Ile Leu Pro Pro Thr Asn Val Gly
            20                  25                  30
Ser Asn Thr Tyr
        35

( 2 ) INFORMATION FOR SEQ ID NO:21:

( i ) SEQUENCE CHARACTERISTICS:
  ( A ) LENGTH: 37 amino acids
  ( B ) TYPE: amino acid
  ( C ) STRANDEDNESS: single
  ( D ) TOPOLOGY: linear ( i i ) MOLECULE TYPE: peptide ( i x ) FEATURE:
  ( D ) OTHER INFORMATION: disulfide bridge between the Cys residues at positions 2 and 7; amidated Tyr at position 37

( x i ) SEQUENCE DESCRIPTION: SEQ ID NO:21:

Lys Cys Asn Thr Ala Thr Cys Ala Thr Gln Arg Leu Ala Asn Phe Leu
1               5                   10                  15
Ile Arg Ser Ser Asn Asn Leu Gly Ala Ile Leu Ser Ser Thr Asn Val
            20                  25                  30
Gly Ser Asn Thr Tyr
        35

( 2 ) INFORMATION FOR SEQ ID NO:22:

( i ) SEQUENCE CHARACTERISTICS:
  ( A ) LENGTH: 37 amino acids
  ( B ) TYPE: amino acid
  ( C ) STRANDEDNESS: single
  ( D ) TOPOLOGY: linear ( i i ) MOLECULE TYPE: peptide ( i x ) FEATURE:
  ( D ) OTHER INFORMATION: disulfide bridge between the Cys residues at positions 2 and 7; amidated Tyr at position 37

( x i ) SEQUENCE DESCRIPTION: SEQ ID NO:22:

Lys Cys Asn Thr Ala Thr Cys Ala Thr Gln Arg Leu Ala Asn Phe Leu
1               5                   10                  15
Ile Arg Ser Ser Asn Asn Leu Gly Ala Val Leu Ser Pro Thr Asn Val
            20                  25                  30
Gly Ser Asn Thr Tyr
        35

( 2 ) INFORMATION FOR SEQ ID NO:23:

( i ) SEQUENCE CHARACTERISTICS:
        ( A ) LENGTH: 37 amino acids
        ( B ) TYPE: amino acid
        ( C ) STRANDEDNESS: single
        ( D ) TOPOLOGY: linear ( i i ) MOLECULE TYPE: None ( i x ) FEATURE:
        ( D ) OTHER INFORMATION: disulfide bridge between the Cys
            residues at positions 2 and 7;
            amidated Tyr at position 37

( x i ) SEQUENCE DESCRIPTION: SEQ ID NO:23:

```
Lys Cys Asn Thr Ala Thr Cys Ala Thr Gln Arg Leu Ala Asn Phe Leu
 1               5                   10                  15
Ile Arg Ser Ser Asn Asn Leu Gly Pro Val Leu Pro Pro Thr Asn Val
            20                  25                  30
Gly Ser Asn Thr Tyr
            35
```

( 2 ) INFORMATION FOR SEQ ID NO:24:

( i ) SEQUENCE CHARACTERISTICS:
        ( A ) LENGTH: 37 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( D ) OTHER INFORMATION: disulfide bridge between the Cys
            residues at positions 2 and 7;
            amidated Tyr at position 37

( x i ) SEQUENCE DESCRIPTION: SEQ ID NO:24:

```
Lys Cys Asn Thr Ala Thr Cys Ala Thr Gln Arg Leu Thr Asn Phe Leu
 1               5                   10                  15
Val His Ser Ser His Asn Leu Gly Ala Ala Leu Leu Pro Thr Asp Val
            20                  25                  30
Gly Ser Asn Thr Tyr
            35
```

( 2 ) INFORMATION FOR SEQ ID NO:25:

( i ) SEQUENCE CHARACTERISTICS:
        ( A ) LENGTH: 37 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( D ) OTHER INFORMATION: disulfide bridge between the Cys
            residues at positions 2 and 7;
            amidated Tyr at position 37

( x i ) SEQUENCE DESCRIPTION: SEQ ID NO:25:

```
Lys Cys Asn Thr Ala Thr Cys Ala Thr Gln Arg Leu Thr Asn Phe Leu
 1               5                   10                  15
Val His Ser Ser His Asn Leu Gly Ala Ala Leu Ser Pro Thr Asp Val
            20                  25                  30
Gly Ser Asn Thr Tyr
            35
```

( 2 ) INFORMATION FOR SEQ ID NO:26:

( i ) SEQUENCE CHARACTERISTICS:
        ( A ) LENGTH: 36 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( D ) OTHER INFORMATION: disulfide bridge between the Cys
        residues at positions 1 and 6;
        amidated Tyr at position 36

( x i ) SEQUENCE DESCRIPTION: SEQ ID NO:26:

```
Cys Asn Thr Ala Thr Cys Ala Thr Gln Arg Leu Thr Asn Phe Leu Val
1               5                   10                  15
His Ser Ser His Asn Leu Gly Ala Ala Leu Pro Ser Thr Asp Val Gly
                20                  25                  30
Ser Asn Thr Tyr
            35
```

( 2 ) INFORMATION FOR SEQ ID NO:27:

( i ) SEQUENCE CHARACTERISTICS:
        ( A ) LENGTH: 37 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( D ) OTHER INFORMATION: disulfide bridge between the Cys
        residues at positions 2 and 7;
        amidated Tyr at position 37

( x i ) SEQUENCE DESCRIPTION: SEQ ID NO:27:

```
Lys Cys Asn Thr Ala Thr Cys Ala Thr Gln Arg Leu Thr Asn Phe Leu
1               5                   10                  15
Val Arg Ser Ser His Asn Leu Gly Ala Ala Leu Ser Pro Thr Asp Val
                20                  25                  30
Gly Ser Asn Thr Tyr
            35
```

( 2 ) INFORMATION FOR SEQ ID NO:28:

( i ) SEQUENCE CHARACTERISTICS:
        ( A ) LENGTH: 37 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( D ) OTHER INFORMATION: disulfide bridge between the Cys
        residues at positions 2 and 7;
        amidated Tyr at position 37

( x i ) SEQUENCE DESCRIPTION: SEQ ID NO:28:

```
Lys Cys Asn Thr Ala Thr Cys Ala Thr Gln Arg Leu Thr Asn Phe Leu
1               5                   10                  15
Val Arg Ser Ser His Asn Leu Gly Ala Ile Leu Pro Pro Thr Asp Val
                20                  25                  30
Gly Ser Asn Thr Tyr
            35
```

( 2 ) INFORMATION FOR SEQ ID NO:29:

( i ) SEQUENCE CHARACTERISTICS:
        ( A ) LENGTH: 37 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( D ) OTHER INFORMATION: disulfide bridge between the Cys
        residues at positions 2 and 7;
        amidated Tyr at position 37

( x i ) SEQUENCE DESCRIPTION: SEQ ID NO:29:

Lys Cys Asn Thr Ala Thr Cys Ala Thr Gln Arg Leu Thr Asn Phe Leu
            5                      10                   15

Val Arg Ser Ser His Asn Leu Gly Pro Ala Leu Pro Pro Thr Asp Val
            20                      25                   30

Gly Ser Asn Thr Tyr
            35

( 2 ) INFORMATION FOR SEQ ID NO:30:

( i ) SEQUENCE CHARACTERISTICS:
        ( A ) LENGTH: 25 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( D ) OTHER INFORMATION: acetylated Val at position 1;
        amidated Tyr at position 25

( x i ) SEQUENCE DESCRIPTION: SEQ ID NO:30:

Val Leu Asn Lys Leu Ser Gln Glu Leu His Lys Leu Gln Thr Tyr Pro
1               5                    10                15

Arg Thr Asn Thr Gly Ser Gly Thr Tyr
            20                      25

METHODS FOR REGULATING GASTROINTESTINAL MOTILITY

RELATED APPLICATIONS

This is a division of application Ser. No. 08/302,069, filed Sep. 7, 1994 which is a continuation-in-part application Ser. No. 08/118,381, filed Sep. 7, 1993.

FIELD OF THE INVENTION

The present invention relates to methods for regulating gastrointestinal motility. More particularly, the invention relates to the use of amylin and agonists of amylin in the treatment of disorders which would be benefited with agents useful in delaying and/or slowing gastric emptying. The invention also relates to the use of amylin antagonists to accelerate gastric emptying, for example, in treating gastric hypomotility and associated disorders.

BACKGROUND

Amylin

Amylin is a 37-amino acid protein hormone. It was isolated, purified and chemically characterized as the major component of amyloid deposits in the islets of pancreases of human Type 2 diabetics (Cooper et al., Proc. Natl. Acad. Sci., USA, 84:8628–8632 (1987)). The amylin molecule has two important post-translational modifications: the C-terminus is amidated, and the cysteines in positions 2 and 7 are cross-linked to form an N-terminal loop. The sequence of the open reading frame of the human amylin gene shows the presence of the Lys-Arg dibasic amino acid proteolytic cleavage signal, prior to the N-terminal codon for Lys, and the Gly prior to the Lys-Arg proteolytic signal at the CLAIMS-terminal position, a typical sequence for amidation by protein amidating enzyme, PAM (Cooper et al., Biochem. Biophys. Acta, 1014:247–258 (1989)). Amylin is the subject of United Kingdom patent application Serial No. 8709871, filed Apr. 27, 1987, and corresponding U.S. applications filed Apr. 27, 1988, Nov. 23, 1988 and May 2, 1989.

In Type 1 diabetes, amylin has been shown to be deficient and combined replacement with insulin has been proposed as a preferred treatment over insulin alone, for instance in limiting hypoglycemic episodes. The use of amylin for the treatment of diabetes mellitus is the subject of United Kingdom patent application Serial No. 8720115 filed on Aug. 26, 1987, by G. J. S. Cooper, and filed as patent application Ser. No. 236,985 in the United States on Aug. 26, 1988. Pharmaceutical compositions containing amylin and amylin plus insulin are described in U.S. Pat. No. 5,124,314, issued Jun. 23, 1992.

Excess amylin action mimics key features of Type 2 diabetes and amylin blockade has been proposed as a novel therapeutic strategy. It has been disclosed in commonly-owned copending U.S. patent application Ser. No. 275,475, filed Nov. 23, 1988 by Cooper, G. J. S. et al., the contents of which are incorporated herein by reference, that amylin causes reduction in both basal and insulin-stimulated incorporation of labelled glucose into glycogen in skeletal muscle. The latter effect was also disclosed to be shared by CGRP (see also Leighton, B. and Cooper, G. J. S., Nature, 335:632–635 (1988)). Amylin and CGRP were approximately equipotent, showing marked activity at 1 to 10 nM. Amylin is also reported to reduce insulin-stimulated uptake of glucose into skeletal muscle and reduce glycogen content (Young et al., Amer. J. Physiol. 259:457-46-1 (1990)). The treatment of Type 2 diabetes and insulin resistance with amylin antagonists is disclosed.

Both the chemical structure and the gene sequence of amylin have been said to support the determination that it is a biologically active or "messenger" molecule. The chemical structure is nearly 50% identical to the calcitonin-gene-related peptides (CGRP), also 37 amino acid proteins which are widespread neurotransmitters with many potent-biological actions, including vasodilation. Amylin and CGRP share the $^2$Cys–$^7$Cys disulphide bridge and the C-terminal amide, both of which are essential for full biologic activity (Cooper et al. Proc. Natl. Acad. Sci., 85–7763–7766 (1988)).

Amylin may be one member of a family of related peptides which include CGRP, insulin, insulin-like growth factors, and the relaxins and which share common genetic heritage (Cooper, G. J. S., et al., Prog. Growth Factor Research 1:99–105 (1989)). The two peptides calcitonin and CGRP-1 share common parentage in the calcitonin gene where alternative processing of the primary mRNA transcript leads to the generation of the two distinct peptides, which share only limited sequence homology (about 30%) (Amara, S. G. et al., Science, 229:1094–1097 (1985)). The amylin gene sequence is typical for a secreted messenger protein, with the MRNA coding a prepropeptide with processing sites for production of the secreted protein within the Golgi or secretary granules. Amylin is mainly co-localized with insulin in beta cell granules and may share the proteolytic processing enzymes that generate insulin from proinsulin.

Amylin is primarily synthesized in pancreatic beta cells and is secreted in response to nutrient stimuli such as glucose and arginine. Studies with cloned beta-cell tumor lines (Moore et al., Biochem. Biophys. Res. Commun., 179(1) (1991)), isolated islets (Kanatsuka et al., FEBS Lett., 259(1), 199–201 (1989)) and perfused rat pancreases (Ogawa et al., J. Clin. Invest., 85:973–976 (1990)) have shown that short pulses, 10 to 20 minutes, of nutrient secretagogues such as glucose and arginine, stimulate release of amylin as well as insulin. The molar amylin:insulin ratio of the secreted proteins varies between preparations from about 0.01 to 0.4, but appears not to vary much with different stimuli in any one preparation. However, during prolonged stimulation by elevated glucose, the amylin:insulin ratio can progressively increase (Gedulin et al., Biochem. Biophys. Res. Commun., 180(1):782–789 (1991)). Thus, perhaps because gene expression and rate of translation are independently controlled, amylin and insulin are not always secreted in a constant ratio.

Amylin-like immunoreactivity has been measured in circulating blood in rodents and humans by a variety of radioimmunoassays all of which use rabbit anti-amylin antiserum, and most of which use an extraction and concentration procedure to increase assay sensitivity. In normal humans, fasting amylin levels from 1 to 10 pM and post-prandial or post-glucose levels of 5 to 20 pM have been reported (e.g., Hartter et al., Diabetologia, 34:52–54 (1991)); Sanke et al., Diabetologia, 34:129–132 (1991)); Koda et al., The Lancet, 339:1179–1180 (1992)). In obese, insulin-resistant individuals, post-food amylin levels can go higher, reaching up to about 50 pM. For comparison, the values for fasting and post-prandial insulin are 20 to 50 pM, and 100 to 300 pM respectively in healthy people, with perhaps 3-to 4-fold higher levels in insulin-resistant people. In Type 1 diabetes, where beta-cells are destroyed, amylin levels are at or below the levels of detection and do not rise in response to glucose (Koda et al., The Lancet, 339, 1179–1180 (1992)). In normal mice and rats, basal amylin levels have been reported from 30 to 100 pM, while values up to 600 pM have been measured in certain insulin-resistant, diabetic strains of rodents (e.g., Huang et al., *Hypertension*, 19:I-101-I-109 (1992); Gill et al., *Life Sciences*, 48:703–710 (1991)).

It has been discovered that certain actions of amylin are similar to known non-metabolic actions of CGRP and calcitonin; however, the metabolic actions of amylin discovered during investigations of this newly identified protein appear to reflect its primary biologic role. At least some of these metabolic actions are mimicked by CGRP, albeit at doses which are markedly vasodilatory (see, e.g., Leighton et al., *Nature*, 335:632–635 (1988); Molina et al., *Diabetes*, 39:260–265 (1990)).

The first discovered action of amylin was the reduction of insulin-stimulated incorporation of glucose into glycogen in rat skeletal muscle (Leighton et al., *Nature*, 335:632–635 (1988)); the muscle was made "insulin-resistant". Subsequent work with rat soleus muscle ex-vivo and in vitro has indicated that amylin reduces glycogen-synthase activity, promotes conversion of glycogen phosphorylase from the inactive b form to the active a form, promotes net loss of glycogen (in the presence or absence of insulin), increases glucose-6-phosphate levels, and can increase lactate output (see, e.g., Deems et al., *Biochem. Biophys. Res. Commun.*, 181(1):116–120 (1991)); Young et al., *FEBS Letts*, 281(1, 2):149–151 (1991)). Whether amylin interferes with glucose transport per se is uncertain (see e.g. Young et al., *Am. J. Physiol.*, 259:E457–E461 (1990); Zierath et al., *Diabetologia*, 35:26–31 (1992)). Studies of amylin and insulin dose-response relations show that amylin acts as a noncompetitive or functional antagonist of insulin in skeletal muscle (Young et al., *Am. J. Physiol., Am. J. Physiol.*, 263(2):E274–E281 (1992)). There is no evidence that amylin interferes with insulin binding to its receptors, or the subsequent activation of insulin receptor tyrosine kinase (Follett et al., *Clinical Research* 39(1):39A (1991); Koopmans et al., *Diabetologia*, 34, 218–224 (1991)). The actions of amylin on skeletal muscle resemble those of adrenalin (epinephrine). However, while adrenalin's actions are believed to be mediated largely by cAMP, some workers have concluded that amylin's actions are not mediated by cAMP (see Deems et al., *Biochem. Biophys. Res. Commun.*, 181(1):116–120 (1991)), while still others report that amylin does activate adenyl cyclase and increases cAMP in skeletal muscle (Moore and Rink, *Diabetes* 42:5,821 June (1993)), consistent with transduction of its effect on glycogen metabolism via cAMP-dependent protein kinase phosphorylation of synthase and phosphorylase.

It is believed that amylin acts through receptors present in plasma membranes. It has been reported that amylin works in skeletal muscle via a receptor-mediated mechanism that promotes glycogenolysis, by activating the rate-limiting enzyme for glycogen breakdown, phosphorylase a (Young, A. et al., *FEBS Letts.*, 281:149–151 (1991)). Studies of amylin and CGRP, and the effect of the antagonist $^{8-37}$CGRP, suggest that amylin acts via its own receptor (Wang et al., *FEBS Letts.*, 219:195–198 (1991 b)), counter to the conclusion of other workers that amylin may act primarily at CGRP receptors (e.g., Chantry et al., *Biochem. J.*, 277:139–143 (1991); Galeazza et al., *Peptides*, 12:585–591 (1991); Zhu et al., *Biochem. Biophys. Res. Commun.*, 177(2):771776 (1991)). Recently, amylin receptors and their use in various methods for screening and assaying for amylin agonist and antagonist compounds were described in International Application Number PCT/US92/02125, published Oct. 1, 1992, and titled "Receptor-Based Screening Methods for Amylin, Agonists and Antagonists."

While amylin has marked effects on hepatic fuel metabolism in vivo, there is no general agreement as to what amylin actions are seen in isolated hepatocytes or perfused liver. The available data do not support the idea that amylin promotes hepatic glycogenolysis, i.e., it does not act like glucagon (e.g., Stephens, et al., *Diabetes*, 40:395–400 (1991)); Gomez-Foix et al., *Biochem J.*, 276:607–610 (1991)). It has been suggested that amylin may act on the liver to promote conversion of lactate to glycogen and to enhance the amount of glucose able to be liberated by glucagon (see Roden et al., *Diabetologia*, 35:116–120 (1992)). Thus, amylin could act as an anabolic partner to insulin in liver, in contrast to its catabolic action in muscle.

The effect of amylin on regional hemodynamic actions, including renal blood flow, in conscious rats was recently reported (Gardiner et al., *Diabetes*, 40:948–951 (1991)). The authors noted that infusion of rat amylin was associated with greater renal vasodilation and less mesenteric vasoconstriction than is seen with infusion of human α-CGRP. They concluded that, by promoting renal hyperemia to a greater extent than did α-CGRP, rat amylin could cause less marked stimulation of the renin-angiotensin system, and thus, less secondary angiotensin II-mediated vasoconstriction. It was also noted, however, that during coninfusion of human α-$^{8-37}$ CGRP [SEQ. ID. NO.1] and rat amylin renal and mesenteric vasoconstrictions were unmasked, presumably due to unopposed vasoconstrictor effects of angiotensin II, and that this finding is similar to that seen during coinfusion of human A-CGRP and human α-$^{8-37}$ CGRP (id. at 951).

In fat cells, contrary to its adrenalin-like action in muscle, amylin has no detectable actions on insulin-stimulated glucose uptake, incorporation of glucose into triglyceride, $CO_2$ production (Cooper et al., *Proc. Natl. Acad. Sci.*, 85:7763–7766 (1988)) epinephrine-stimulated lipolysis, or insulin-inhibition of lipolysis (Lupien J. R., and Young, A. A., "Diabetes Nutrition and metabolism—Clinical and Experimental", Vol. 6(1), pages 13–18 (February 1993)). Amylin thus exerts tissue-specific effects, with direct action on skeletal muscle, marked indirect (via supply of substrate) and perhaps direct effects on liver, while adipocytes appear "blind" to the presence or absence of amylin. No direct effects of amylin on kidney tissue have been reported.

It has also been reported that amylin can have marked effects on secretion of insulin. In isolated islets (Ohsawa et al., *Biochem. Biophys. Res. Commun.*, 160(2):961–967 (1989)), in the perfused pancreas (Silvestre et al., *Reg. Pept.*, 31-23-31 (1990), and in the intact rat (Young et al., *Mol. Cell. Endocrinol.*, 84:R1–R5 (1992)), some experiments indicate that amylin down-regulates insulin secretion. The perfused pancreas experiments point to selective down-regulation of the secretary response to glucose with sparing of the response to arginine. Other workers, however, have been unable to detect effects of amylin on isolated β-cells, on isolated islets, or in the whole animal (see Broderick et al., *Biochem. Biophys. Res. Comm.*, Vol. 177:932–938 (1991) and references therein).

The most striking effect of amylin in vivo is stimulation of a sharp rise in plasma lactate, followed by a rise in plasma glucose (Young et al., *FEBS Letts*, 281(1,2):149–151 (1991)). Evidence indicates that the increased lactate provides substrate for glucose production and that amylin actions can occur independent of changes in insulin or glucagon. In "glucose clamp" experiments, amylin infusions cause "insulin resistance," both by reducing peripheral glucose disposal, and by limiting insulin-mediated suppression of hepatic glucose output (e.g., Frontoni et al., *Diabetes*, 40:568–573 (1991); Koopmans et al., *Diabetologia*, 34, 218–224 (1991)).

In lightly anesthetized rats which were fasted for 18 hours to deplete their stores of hepatic glycogen, amylin injections stimulated rises in plasma lactate from about 0.5 to 1.5 mM followed by a prolonged increase in plasma glucose levels from about 6 to 11 mM. These effects were observed for both intravenous and subcutaneous injections (Young et al., *FEBS Letts.*, 281(1.2):149-151 (1991)). The effects of amylin in fed animals differ quantitatively from its effects in fasted animals. In fed rats, with presumably normal liver glycogen stores, amylin causes a more pronounced and prolonged rise in plasma lactate; however, there is only a modest rise in plasma glucose. It has been suggested that amylin promotes the "return limb" of the Cori cycle, i.e., muscle glycogen via breakdown to lactate provides substrate for hepatic gluconeogenesis and glycogen production and probably triglyceride synthesis. Insulin drives the forward limb, i.e., uptake of glucose into muscle and production of muscle glycogen. Insulin and amylin can thus be seen as partners in regulating the "indirect" pathway of postprandial hepatic glycogen repletion. "Insulin resistance" in muscle and liver may be under normal, physiologic regulation by amylin.

Non-metabolic actions of amylin include vasodilator effects which may be mediated by interaction with CGRP vascular receptors. Reported in vivo tests suggest that amylin is at least about 100 to 1000 times less potent than CGRP as a vasodilator (Brain et al., *Eur. J. Pharmacol.*, 183:2221 (1990); Wang et al., *FEBS Letts.*, 291:195-198 (1991)). Injected into-the brain, amylin has been reported to suppress food intake (e.g., Chance et al., *Brain Res.*, 539, 352-354 (1991)), an action shared with CGRP and calcitonin. The effective concentrations at the cells that mediate this action are not known. Amylin has also been reported to have effects both on isolated osteoclasts where it caused cell quiescence, and in vivo where it was reported to lower plasma calcium by up to 20% in rats, in rabbits, and in humans with Paget's disease (see, e.g., Gilbey et al., *J. Bone Mineral Res.*, S293 (1991). From the available data, amylin seems to be 10 to 30 times less potent than human calcitonin for these actions. Interestingly, it was reported that amylin appeared to increase osteoclast cAMP production but not to increase cytosolic $Ca^{2+}$, while calcitonin does both (Alam et al., *Biochem. Biophys. Res. Commun.*, 179(1):134-139 (1991)). It was suggested, though not established, that calcitonin may act via two receptor types and that amylin may interact with one of these.

Infusing amylin receptor antagonists may be used to alter glucoregulation. $^{8-37}$CGRP is a demonstrated amylin blocker in vitro and in vivo (Wang et al., *Biochem. Biophys. Res. Commun.*, 181(3):1288-1293 (1991)), and was found to alter glucoregulation following an arginine infusion in fed rats (Young et al., *Mol. Cell. Endocrinol.*, 84:R1-R5 (1992)). The initial increase in glucose concentration is attributed to arginine-stimulated glucagon secretion from islet alpha cells; the subsequent restoration of basal glucose is attributed to insulin action along with changes in other glucoregulatory hormones. When the action of amylin is blocked by preinfusion of $^{8-37}$hCGRP, the initial glucose increase is not significantly different, but there is a subsequent fall in glucose concentration to well below the basal level, which is restored only after some 80 minutes. Thus, glucoregulation following this challenge with an islet secretagogue was altered by infusion of an amylin receptor antagonist. Additionally, insulin concentrations were measured at half hour intervals and it was found that insulin concentration 30 minutes following the arginine infusion was almost twice as high in animals infused with an amylin receptor antagonist as in the normal controls. $^{8-37}$CGRP is also an effective CGRP antagonist. However, very similar results were seen with another amylin antagonist, AC66, which is selective for amylin receptors compared with CGRP receptors (Young et al., *Mol. Cell. Endocrino.*, 84:R1-R5 (1992)). These results are said to support the conclusion that blockade of amylin action can exert important therapeutic benefits in Type 2 diabetes.

Patients with Type 1 diabetes, in addition to a lack of insulin, are reported to have marked amylin deficiency. As noted above, data show that amylin expression and secretion by pancreatic beta-cells is absent or well below normal in Type 1 diabetes. In several animal models of Type 1 diabetes, amylin secretion and gene expression are depressed (Cooper et al., *Diabetes*, 497-500 (1991); Ogawa et al., *J. Clin. Invest.*, 85:973-976 (1990)). Measurements of plasma amylin in Type 1 diabetic patients show that amylin is deficient in these patients after an overnight fast, and that a glucose load does not elicit any increase in amylin levels (Koda et al., *The Lancet*, 339:1179-1180 (1992)).

It has also been discovered that, surprisingly in view of its previously described renal vasodilator and other properties, amylin markedly increases plasma renin activity in intact rats when given subcutaneously in a manner that avoids any disturbance of blood pressure. This is important because lowered blood pressure is a strong stimulus to renin release. Amylin antagonists, such as amylin receptor antagonists, including those selective for amylin receptors compared to CGRP and/or calcitonin receptors, can be used to block the amylin-evoked rise of plasma renin activity. These unexpected findings support the determination that amylin antagonists will reduce plasma renin activity with consequent therapeutic benefit in hypertension and cardiac failure and other disorders associated with elevated, inappropriate or undesired renin activity. Moreover, the additional ability of amylin antagonists to favorably modulate insulin resistance and other common metabolic disorders frequently associated with hypertension and cardiac disease provides a particularly desirable therapeutic profile.

Gastric Hypomotility

Gastric hypomotility with delayed emptying of liquid and/or solid contents is a component of a number of gastrointestinal disorders. For a general discussion, see *Goodman and Gilman's The Pharmacological Basis of Therapeutics*, Chapter 38 (Pergamon Press, Eighth Edition 1990). The symptoms of such disorders may include nausea, vomiting, heartburn, postprandial discomfort, and indigestion. Gastroesophageal reflux is often evident and can give rise to esophageal ulceration; there may also be respiratory symptoms or intense substernal pain that can be confused with asthma or myocardial infarction, respectively. Although the cause is unknown in the majority of patients, gastric stasis or hypomotility is frequently a consequence of diabetic neuropathy; this condition is also often present in patients with anorexia nervosa or achlorhydria or following gastric surgery. Id. at page 928.

The medical management of patients with gastric hypomotility usually includes the administration of a prokinetic agent. Although antiemetic phenothiazines or bethanechol may provide some relief, these drugs do not accelerate gastric emptying in the vast majority of patients and often produce unacceptable side effects. At present, available prokinetic agents include metoclopramide and cisapride, but others (e.g., domperidone) are being evaluated. Id.

Metoclopramide decreases receptive relaxation in the upper portion of the stomach and increases antral contractions. The pylorus and duodenum are relaxed, while the tone of the lower esophageal sphincter is enhanced. These effects combine to accelerate the emptying of gastric contents and to reduce reflux from the duodenum and the stomach into the esophagus. In addition, the transit time of material from the duodenum to the ileocecal valve is reduced as a result of increased jejunal peristalsis. Metoclophramide has little effect on gastric secretion or colonic motility. Id. at page 928.

In general, dopaminergic agonists produce the opposite pattern of effects, and these are mediated by $D_2$ receptors that are located, at least in part, within the gastrointestinal tract. Id.

The mechanism of action of metoclopramide is poorly understood, even though it is clearly a dopaminergic antagonist and can block the gastrointestinal effects caused by the local or systemic administration of dopaminergic agonists. Although vagotomy does not abolish the effects of metoclopramide, its prokinetic actions can be blocked by atropine or other muscarinic antagonists. Moreover, not all dopaminergic antagonists speed gastric emptying. It is thought that the drug promotes the release of acetylcholine from myenteric neurons, although direct evidence of this action is lacking. Since bethanechol can enhance the effects of metoclopramide, enhanced responsiveness to acetylcholine may also be involved. Id. at pages 928–929.

Domperidone is a derivative of benzimidazole that possesses both prokinetic and antiemetic properties. It is a dopaminergic antagonist, and it produces marked hyperprolactinemia; its effects on gastrointestinal motility also closely resemble those of metoclopramide. However, unlike metoclopramide, these effects are not antagonized by atropine; and explanation for this difference has not yet been advanced. Domperidone crosses the blood-brain barrier to only a limited extent, and it causes extrapyramidal side effects only rarely. As a result, it does not interfere with the treatment of Parkinson's disease, and it may be useful in counteracting the gastrointestinal disturbances caused by levodopa and bromocriptine. Thus far, the drug appears to have the same therapeutic utility as metoclopramide in the treatment of patients with gastric hypomotility. However, it has less antiemetic activity. Id. at page 929. Domperidone appears to be rapidly absorbed after oral administration, but its bioavailability is only about 15%; most of the drug and its metabolites are excreted in the feces. The half-time for its elimination from plasma is about 7 to 8 hours. Id. Domperidone is not generally available in the United States; it is available elsewhere as MOTILIUM. Optimal dosage has not been established, but daily oral doses of 40 to 120 mg have been utilized in the treatment of gastric hypomotility. Id. at page 929.

Cisapride is a benzamide and its effects on the motility of the stomach and small bowel closely resemble those of metoclopramide and domperidone; however, unlike these drugs, it also increases colonic motility and can cause diarrhea. The mechanism of its gastrointestinal actions is poorly understood. Like metoclopramide, these actions are blocked by atropine and may involve the release of myenteric acetylcholine. Cisapride appears to be devoid of dopaminergic blocking activity, and it does not influence the concentration of prolactin in plasma or cause extrapyramidal symptoms. The drug binds to and blocks 5-$HT_2$ tryptaminergic receptors in the rat ileum, but the relationship of this action to its effects in man has not been established. Id. Thus far the efficacy of the drug in the treatment of disorders of gastric hypomotility appears to equal those of metoclopramide and domperidone without the side effects that result from dopaminergic blockage. In additional, cisapride may be useful in the treatment of patients with chronic idiopathic constipation or with colonic hypomotility due to spinal cord injury. Id. at page 929.

In contrast to the above, agents which serve to-delay gastric emptying have found a place in medicine as well, particularly as diagnostic aids in gastro-intestinal radiologic examinations. For example, glucagon is a polypeptide hormone which is produced by the alpha cells of the pancreatic islets of Langerhans. It is a hyperglycaemic agent which mobilizes glucose by activating hepatic glycogenolysis. It can to a lesser extent stimulate the secretion of pancreatic insulin. Glucagon is administered as glucagon hydrochloride; doses are usually expressed as glucagon.

Glucagon is used in the treatment of insulin-induced hypoglycaemia when administration of glucose intravenously is not possible. It is given by subcutaneous, intramuscular, or intravenous injection in a dose of 0.5 to 1 mg (unit), repeated if necessary after 20 minutes. However, as glucagon reduces the motility of the gastro-intestinal tract it is used as a diagnostic aid in gastro-intestinal radiological examinations. The route of administration is dependent upon the diagnostic procedure. A dose of 1 to 2 mgs (units) administered intramuscularly has an onset of action of 4 to 14 minutes and a duration of effect of 10 to 40 minutes; 0.2 to 2 mgs (units) given intravenously produces an effect within one minute that lasts for 9 to 25 minutes.

Glucagon has been used in several studies to treat various painful gastro-intestinal disorders associated with spasm. Daniel et al. (Br. Med. J., 1974, 3, 720) reported quicker symptomatic relief of acute diverticulitis in patients treated with glucagon compared with those who had been treated with analgesics or antispasmodics. A review by Glauser et al., (J. Am. Coll. Emergency Physns, 1979, 8, 228) described relief of acute oesophageal food obstruction following gulcagon therapy. In another study glucagon significantly relieved pain and tenderness in 21 patients with biliary tract disease compared with 22 patients treated with placebo (M. J. Stower et al., Br. J. Surg., 1982, 69, 591–2). Franken et al., however, (Radiology, 1983, 146, 687) failed to show any advantage of glucagon over placebo in the hydrostatic reduction of ileocolic intussusception in a study of 30 children, and Webb et al. (Med. J. Aust., 1986, 144, 124) concluded that glucagon was ineffective in the management of ureteric colic in a casualty department.

SUMMARY OF THE INVENTION

We have now discovered that, surprisingly in view of its previously described hyperglycemic properties, amylin and amylin agonists, including as those described herein, for example, the amylin agonist analogue $^{25,28,29}$Pro-h-amylin [SEQ. ID. NO.2] (also referred to as "AC-0137"), can reduce gastric motility and slow gastric emptying, as evidenced by the ability of such compounds to reduce post-prandial plasma glucose levels.

The present invention is directed to novel methods for reducing gastric motility and slowing gastric emptying, comprising the administration of an amylin or an amylin agonist, for example, the amylin agonist analogue AC-0137. These methods will be useful in the treatment of, for example, post-prandial hyperglycemia, a complication associated with type 2 (non-insulin dependent) diabetes mellitus.

The term "amylin" is understood to include compounds such as those defined by Young and Cooper in U.S. Pat. No. 5,234,906, issued Aug. 10, 1993, for "Hyperglycemic Compositions," the contents of which is hereby incorporated by reference. For example, it includes the human peptide hormone, and species variations of it, referred to as amylin and secreted from the beta cells of the pancreas. "Amylin agonists" is also a term known in the art, and refers to compounds which mimic the effects of amylin. Thus, amylin itself and amylin agonist analogues may also be referred to broadly as amylin agonists. The term "amylin agonist analogue" is understood to refer to derivatives of an amylin which act as amylin agonists, normally, it is presently believed, by virtue of binding to or otherwise directly or indirectly interacting with an amylin receptor or other receptor or receptors with which amylin itself may interact to elicit those biological properties referred to above. In addition to those described herein, other useful amylin agonist analogs are identified in an International Application, WPI Acc. No. 93-182488/22, entitled "New Amylin Agonist Peptides Used for Treatment and Prevention of Hypoglycemia and Diabetes Mellitus," the contents of which is also hereby incorporated by reference.

In a first aspect, the invention features a method of beneficially regulating gastrointestinal motility in a subject by administering to said subject a therapeutically effective amount of an amylin or an amylin agonist, preferably an amylin agonist analogue. In one embodiment, the methods of the present invention are directed to reducing gastric motility. In another embodiment, the invention is directed to methods of delaying gastric emptying.

These methods may be used on a subject undergoing a gastrointestinal diagnostic procedure, for example radiological examination or magnetic resonance imaging. Alternatively, these methods may be used to reduce gastric motility in a subject suffering from a gastro-intestinal disorder, for example, spasm (which may be associated with acute diverticulitis, a disorder of the biliary tract or a disorder of the Sphincter of Oddi).

In another aspect, the invention is directed to a method of treating post-prandial dumping syndrome in a subject by administering to the subject a therapeutically effective amount of an amylin agonist.

In yet another aspect, the invention is directed to a method of treating post-prandial hyperglycemia by administering to a subject a therapeutically effective amount of an amylin agonist. In a preferred embodiment, the post-prandial hyperglycemia is a consequence of Type 2 diabetes mellitus.

Preferred amylin agonists include $^{25,28,29}$Pro-h-amylin. Preferred amylin agonist analogues also include $^{25,28,29}$Pro-h-amylin.

In another aspect, the present invention is directed to a method of treating gastric hypomotility in a subject by administering to the subject a therapeutically effective amount of an amylin antagonist. In preferred embodiments, these methods may be employed where hypomotility is a consequence of diabetic neuropathy or where hypomotility is a consequence of anorexia nervosa. Hypomotility may also occur as a consequence of achlorhydria or as a consequence of gastric surgery.

In another aspect, the invention is directed to a method of accelerating gastric emptying in a subject by administering to the subject a therapeutically effective amount of an amylin antagonist. By amylin antagonist is meant a compound which interferes with the effects of amylin, for example, a compound that is itself lacks significant pharmacological activity but causes effects by inhibition of action of a specific agonist e.g., by competition for agonist binding sites. Preferably, the amylin antagonist used in these methods is an amylin receptor antagonist. A preferred antagonist is acetyl-$^{11,18}$Arg, $^{30}$Asn, $^{32}$Tyr$^{9-32}$calcitonin (salmon) [SEQ. ID. NO.3].

In another aspect, the invention is directed to a method of treating ingestion of a toxin by administering an amount of an amylin or an amylin agonist effective to prevent or reduce passage of stomach contents to the intestines and aspirating the stomach contents.

indicates the fraction of gastric contents retained in normal and diabetic rats not treated with amylin (different at P<0.001).

Figure 15:
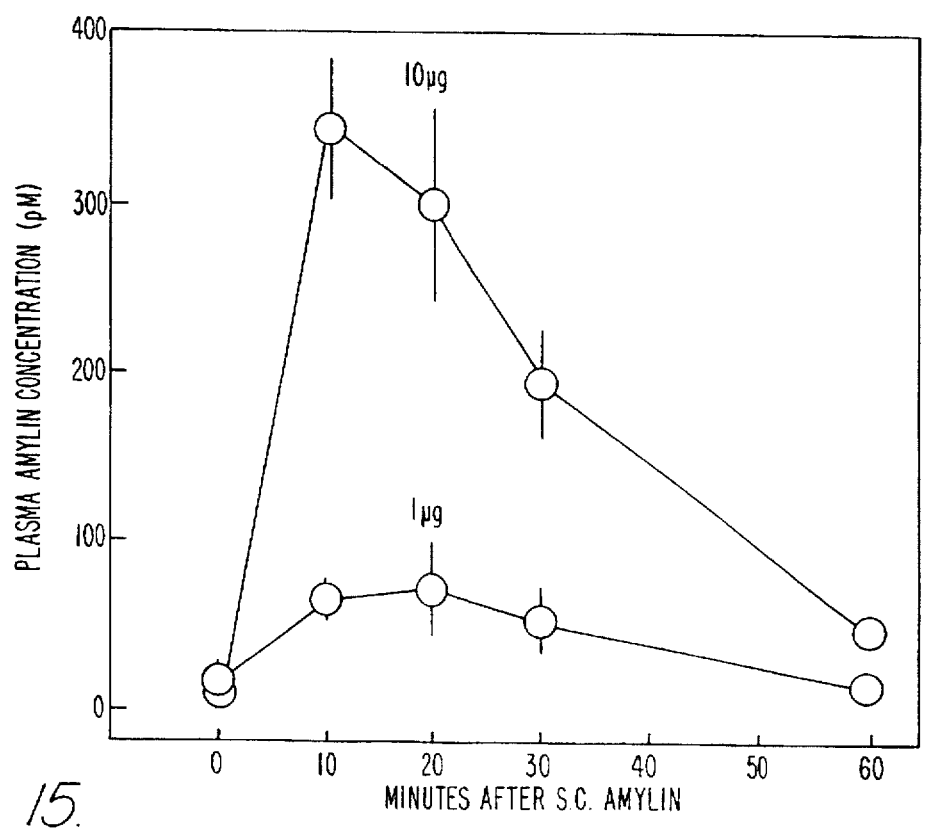

FIG. 15 shows plasma amylin concentration measured after the subcutaneous injection of either 1 μg or 10 μg of synthetic rat amylin (n=3 per group). Symbols are means ± SEM.

Figure 16:
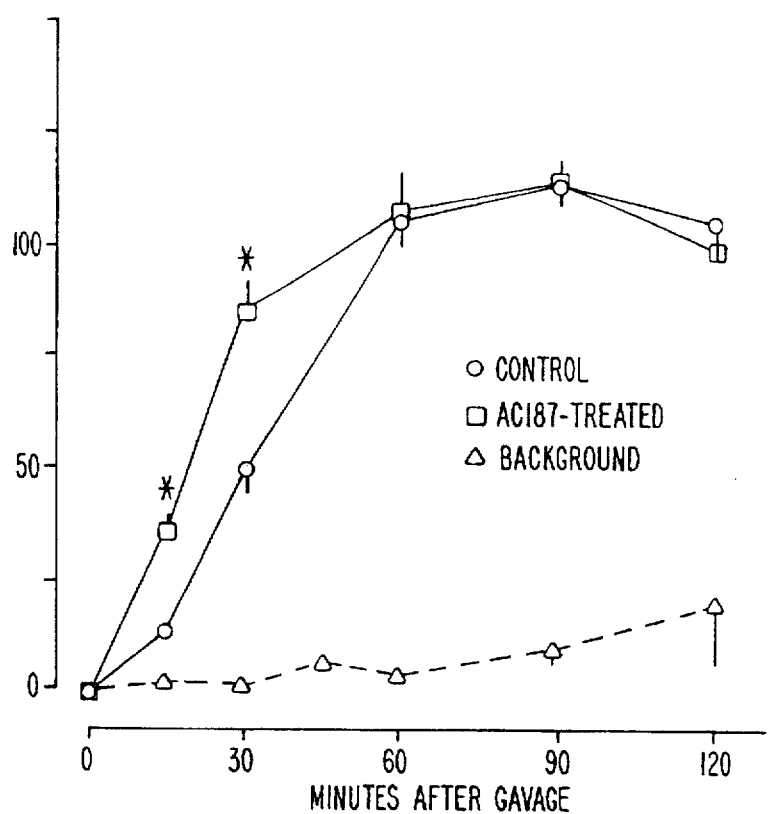

FIG. 16 depicts glucose-derived tritium in plasma (cpm/ 10 μl) after gavage of saline or AC-0187. * indicates statistical significance. The lowest trace (broken line labelled "Background") comes from 4 anesthetized rats gavaged after laparotomy and pyloric ligation. It indicates that little tritium is absorbed directly through the walls of the stomach, and that tritium uptake reflects passage-of glucose into the circulation from the small intestine.

Figure 17:
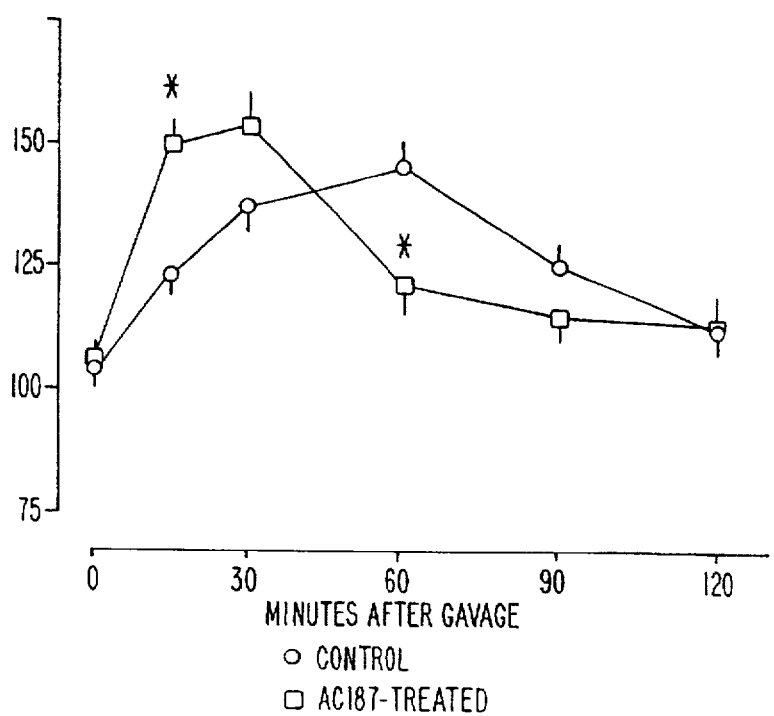

FIG. 17 depicts plasma glucose (mg/dl) post gavage with either saline or AC-0187.

DETAILED DESCRIPTION OF THE INVENTION

The nomenclature of various amylin agonist analogue compounds useful in the present invention can be used to indicate both the peptide that the sequence is based on and the modifications made to any basic peptide amylin sequence, such as human amylin. An amino acid preceded by a superscript number indicates that the named amino acid replaces the amino acid normally present at the amino acid position of the superscript in the basic amino acid sequence. For example, "$^{18}$Arg$^{25,28}$Pro-h-amylin" [SEQ. ID. NO.4] refers to a peptide based on the sequence of "h-amylin" or "human-amylin" having the following substitutions: Arg replacing His at residue 18, Pro replacing Ala at residue 25 and Pro replacing Ser at residue 28. The term "des-$^1$Lys-h-amylin" [SEQ. ID. NO.5] refers to a peptide based on the sequence of human amylin, with the first, or N-terminal, amino acid deleted.

The agonist analogues of amylin of this invention are useful in view of their pharmacological properties. Activity as amylin agonist agents can be indicated by activity in the receptor binding assay and the soleus muscle assay described below. Amylin agonist activity of compounds may also be assessed by the ability to induce hypercalcemia and/or hyperglycemia in mammals, or to reduce postprandial plasma glucose levels, as described herein.

Preferred amylin agonist analogue compounds des-$^1$Lys-h-amylin, $^{28}$Pro-h-amylin [SEQ. ID. NO.6], $^{25,28,29}$Pro-h-amylin, $^{18}$Arg$^{25,28}$Pro-h-amylin, and des-$^1$Lys$^{18}$Arg$^{25,28}$Pro-h-amylin [SEQ. ID. NO.77], all show amylin activity in vivo in treated test animals, provoking marked hyperlactemia followed by hyperglycemia. In addition to having activities characteristic of amylin, certain preferred compounds have also been found to possess more desirable solubility and stability characteristics when compared to human amylin. These preferred compounds include $^{25}$Pro$^{26}$Val$^{28,29}$Pro-h-amylin [SEQ. ID. NO.8], $^{25,28,29}$Pro-h-amylin (also referred to herein as "AC-0137"), and $^{18}$Arg$^{25,28}$Pro-h-amylin.

The method of the present invention can employ an amylin agonist, including amylin or an amylin agonist analogue, for example, amylin receptor agonist analogues such as $^{18}$Arg$^{25,28}$Pro-h-amylin, des-$^1$Lys$^{18}$Arg$^{25,28}$Pro-h-amylin, $^{18}$Arg$^{25,28,29}$Pro-h-amylin [SEQ. ID. NO.9], des-$^1$Lys$^{18}$Arg$^{25,28,29}$Pro-h-amylin [SEQ. ID. NO.10], $^{25,28,29}$Pro-h-amylin, des-$^1$Lys$^{25,228,29}$-Pro-h-amylin [SEQ. ID. NO.11], and $^{25}$Pro$^{26}$Val$^{25,28}$Pro-h-amylin. Examples of other suitable amylin agonist analogues include:

$^{23}$Leu$^{25}$Pro$^{26}$Val$^{28,29}$Pro-h-amylin [SEQ. ID. NO.12];

$^{23}$Leu$^{25}$Pro$^{26}$Val$^{28}$Pro-h-amylin [SEQ. ID. NO.13];

des-$^1$Lys$^{23}$Leu$^{25}$Pro$^{26}$Val$^{28}$Pro-h-amylin [SEQ. ID. NO.14];

$^{18}$Arg$^{23}$Leu$^{25}$Pro$^{26}$Val$^{28}$Pro-h-amylin [SEQ. ID. NO.15];

$^{18}$Arg$^{23}$Leu$^{25,28,29}$Pro-h-amylin [SEQ. ID. NO.16];

$^{18}$Arg$^{23}$Leu$^{25,28}$Pro-h-amylin [SEQ. ID. NO.17];

$^{17}$Ile$^{23}$Leu$^{25,28,29}$Pro-h-amyl in [SEQ. ID. NO.18];

$^{17}$Ile$^{25,28,29}$Pro-h-amylin [SEQ. ID. NO.19];

des-$^1$Lys$^{17}$Ile$^{23}$Leu$^{25,28,29}$Pro-h-amylin [SEQ. ID. NO.20];

$^{17}$Ile$^{18}$Arg$^{23}$Leu-h-amylin [SEQ. ID. NO.21];

$^{17}$Ile$^{18}$Arg$^{23}$Leu$^{26}$Val$^{29}$Pro-h-amylin [SEQ. ID. NO.22];

$^{17}$Ile$^{18}$Arg$^{23}$Leu$^{25}$Pro$^{26}$Val$^{28,29}$Pro-h-amylin [SEQ. ID. NO.23];

$^{13}$Thr$^{21}$His$^{23}$Leu$^{26}$Ala$^{28}$Leu$^{29}$Pro$^{31}$Asp-h-amylin [SEQ. ID. NO.24];

$^{13}$Thr$^{21}$His$^{23}$Leu$^{26}$Ala$^{29}$Pro$^{31}$Asp-h-amylin [SEQ. ID. NO.25];

des-$^1$Lys$^{13}$Thr$^{21}$His$^{23}$Leu$^{26}$Ala$^{28}$Pro$^{31}$Asp-h-amylin [SEQ. ID. NO.26];

$^{13}$Thr$^{18}$Arg$^{21}$His$^{23}$Leu$^{26}$Ala$^{29}$Pro$^{31}$Asp-h-amylin [SEQ. ID. NO.27];

$^{13}$Thr$^{18}$Arg$^{21}$His$^{23}$Leu$^{28,29}$Pro$^{31}$Asp-h-amylin [SEQ. ID. NO.28]; and, $^{13}$Thr$^{18}$Arg$^{21}$His$^{23}$Leu$^{25}$Pro$^{26}$Ala$^{28,29}$Pro$^{31}$Asp-h-amylin [SEQ. ID. NO.29].

Still further amylin agonists including amylin agonist analogues are disclosed in WPI Acc. No. 93-182488/22, "New Amylin Agonist Peptides Used for Treatment and Prevention of Hypoglycemia and Diabetes Mellitus," the disclosure of which has been incorporated by reference.

The activity of amylin agonists may be evaluated using certain biological assays described herein. The receptor binding assay can identify both candidate amylin agonists and antagonists and can be used to evaluate binding, while the soleus muscle assay distinguishes between amylin agonists and antagonists. Effects of amylins or amylin agonists on gastric motility can be identified, evaluated, or screened for using the methods described in the Examples below, or other art-known or equivalent methods for determining gastric motility.

One such method for use in identifying or evaluating the ability of a compound to slow gastric motility, comprises: (a) bringing together a test sample and a test system, said test sample comprising one or more test compounds, and said test system comprising a system for evaluating gastric motility, said system being characterized in that it exhibits, for example, elevated plasma glucose in response to the introduction to said system of glucose or a meal; and, (b) determining the presence or amount of a rise in plasma glucose in said system. Positive and/or negative controls may be used as well. Optionally, a predetermined amount of amylin antagonist (e.g., $^{8-32}$salmon calcitonin) may be added to the test system.

Preferably, agonist compounds exhibit activity in the receptor binding assay on the order of less than about 1 to 5 nM, preferably less than about 1 nM and more preferably less than about 50 pM. In the soleus muscle assay these compounds preferably show EC$_{30}$ values on the order of less than about 1 to 10 micromolar.

The receptor binding assay is described in U.S. patent application Ser. No. 670,231, filed on Mar. 15, 1991, and published on Oct. 1, 1992 as International Application Number PCT/US92/02125, the disclosure of which is incorporated herein by reference. The receptor binding assay is a competition assay which measures the ability of compounds to bind specifically to membrane-bound amylin receptors. A preferred source of the membrane preparations used in the assay is the basal forebrain which comprises membranes from the nucleus accumbens and surrounding regions. Compounds being assayed compete for binding to these receptor preparations with $^{125}$I Bolton Hunter rat amylin. Competition curves, wherein the amount bound (B) is plotted as a function of the log of the concentration of ligand are analyzed by computer, using analyses by nonlinear regression to a 4-parameter logistic equation (Inplot program; GraphPAD Software, San Diego, Calif.) or the ALLFIT program of DeLean et. al. (ALLFIT, Version 2.7 (NIH, Bethesda, Md. 20892)). Munson, P. and Rodbard, D., *Anal. Biochem.* 107:220–239 (1980).

Assays of biological activity of amylin agonists, including amylin agonist analogue preparations in the soleus muscle are performed using previously described methods (Leighton, B. and Cooper, G. J. S., *Nature*, 335:632–635 (1988); Cooper, G. J. S., et al. *Proc. Natl. Acad. Sci. USA* 85:7763–7766 (1988)). In summary, amylin agonist activity is assessed by measuring the inhibition of insulin-stimulated glycogen synthesis in soleus muscle. Amylin antagonist activity is assessed by measuring the resumption of insulin-stimulated glycogen synthesis in the presence of 100 nM rat amylin and an amylin antagonist. Concentrations of peptide dissolved in carrier-free buffers are determined by quantitative amino acid analysis, as described therein. The ability of compounds to act as agonists in this assay is determined by measuring $EC_{50}$ values. Standard errors are determined by fitting of sigmoidal dose response curves using a four parameter logistic equation (De Lean, A., Munson, P. J., Guardabasso, V. and Rodbard, D. (1988) ALLFIT, Version 2.7, National Institute of Child Health and Human Development, N.I.H. Bethesda, Md. 1 diskette). A number of amylin agonists have been characterized using these biological assays. The compounds $^{18}Arg^{25,28}Pro$-h-amylin, des-$^{1}Lys^{18}Arg^{25,28}$, Pro-h-amylin, $^{18}Arg^{25,28,29}Pro$-h-amylin, des-$^{1}Lys^{18}Arg^{25,28,29}Pro$-h-amylin, $^{25,28,29}Pro$-h-amylin, des-$^{1}Lys^{25,28,29}Pro$-h-amylin, and $^{25}Pro^{26}Val^{25,28}Pro$-h-amylin were all found to compete with amylin in the receptor binding assay. These compounds have negligible antagonist activity as measured by the soleus muscle assay and were shown to act as amylin agonists. Similar results were obtained with other agonist compounds listed above.

Amylin antagonist compounds useful in methods of treating gastric hypomotility include the compounds described in U.S. patent application Ser. No. 07/794,288 filed on Nov. 19, 1991, the disclosure of which is hereby incorporated in its entirety by this reference.

Compounds such as those described above are prepared using standard solid-phase peptide synthesis techniques and preferably an automated or semiautomated peptide synthesizer. Typically, an α-N-carbamoyl protected amino acid and an amino acid attached to the growing peptide chain on a resin are coupled at room temperature in an inert solvent such as dimethylformamide, N-methylpyrrolidinone or methylene chloride in the presence of coupling agents such as dicyclohexylcarbodiimide and 1-hydroxybenzotriazole in the presence of a base such as diisopropylethylamine. The α-N-carbamoyl protecting group is removed from the resulting peptide-resin using a reagent such as trifluoroacetic acid or piperidine, and the coupling reaction repeated with the next desired N-protected amino acid to be added to the peptide chain. Suitable N-protecting groups are well known in the art, with t-butyloxycarbonyl (tBoc) and fluorenylmethoxycarbonyl (Fmoc) being preferred herein.

The solvents amino acid derivatives and 4-methylbenzhydryl-amine resin used in the peptide synthesizer were purchased from Applied Biosystems Inc. (Foster City, Calif.), unless otherwise indicated. The side-chain protected amino acids used and purchased from Applied Biosystem, Inc. included the following: Boc-Arg(Mts), Fmoc-Arg(Pmc), Boc-Thr(Bzl), Fmoc-Thr(t-Bu), Boc-Ser (Bzl), Fmoc-Ser(t-Bu), Boc-Tyr(BrZ), Fmoc-Tyr(t-Bu), Boc-Lys(Cl-Z), Fmoc-Lys(Boc), Boc-Glu(Bzl), Fmoc-Glu (t-Bu), Fmoc-His(Trt), Fmoc-Asn(Trt), and Fmoc-Gln(Trt). Boc-His(BOM) was purchased from Applied Biosystems, Inc. or Bachem Inc. (Torrance, Calif.). Anisole, methylsulfide, phenol, ethanedithiol, and thioanisole were obtained from Aldrich Chemical Company (Milwaukee, Wis.). Air Products and Chemicals (Allentown, Pa.) supplied HF. Ethyl ether, acetic acid and methanol were purchased from Fisher Scientific (Pittsburgh, Pa.).

Solid phase peptide synthesis was carried out with an automatic peptide synthesizer (Model 430A, Applied Biosystems Inc., Foster City, Calif.) using the NMP/HOBt (Option 1) system and tBoc or Fmoc chemistry (see, Applied Biosystems User's Manual for the ABI 430A Peptide Synthesizer, Version 1.3B Jul. 1, 1988, section 6, pp. 49–70, Applied Biosystems, Inc., Foster-City, Calif.) with capping. Boc-peptide-resins were cleaved with HF (−5° C. to 0° C. 1 hour). The peptide was extracted from the resin with alternating water and acetic acid, and the filtrates were lyophilized. The Fmoc-peptide resins were cleaved according to standard methods (*Introduction to Cleavage Techniques*, Applied Biosystems, Inc., 1990, pp. 6–12). Some peptides were also assembled using an-Advanced Chem-Tech Synthesizer (Model MPS 350, Louisville, Ky.). Peptides were purified by RP-HPLC (preparative and analytical) using a Waters Delta Prep 3000 system. A C4, C8 or C18 preparative column (10 μ, 2.2×25 cm; Vydac, Hesperia, Calif.) was used to isolate peptides, and purity was determined using a C4, C8 or C18 analytical column (5μ, 0.46×25 cm; Vydac). Solvents (A=0.1% TFA/water and B=0.1% TFA/CH$_3$CN) were delivered to the analytical column at a flowrate of 1.0 ml/min and to the preparative column at 15 ml/min. Amino acid analyses were performed on the Waters Pico Tag system and processed using the Maxima program. The peptides were hydrolyzed by vapor-phase acid hydrolysis (115° C., 20–24 h). Hydrolysates were derivatized and analyzed by standard methods (Cohen, S. A., Meys, M., and Tarrin, T. L. (1989), *The Pico Tag Method: A Manual of Advanced Techniques for Amino Acid Analysis*, pp. 11–52, Millipore Corporation, Milford, Mass.). Fast atom bombardment analysis was carried out by M-Scan, Incorporated (West Chester, Pa.). Mass calibration was performed using cesium iodide or cesium iodide/glycerol. Plasma desorption ionization analysis using time of flight detection was carried out on an Applied Biosystems Bio-Ion 20 mass spectrometer.

Peptide compounds useful in the invention may also be prepared using recombinant DNA techniques, using methods now known in the art. See, e.g., Sambrook et al., *Molecular Cloning: A Laboratory Manual*, 2d Ed., Cold Spring Harbor (1989).

The compounds referenced above form salts with various inorganic and organic acids and bases. Such salts include salts prepared with organic and inorganic acids, for example, HCl, HBr, H$_2$SO$_4$, H$_3$PO$_4$, trifluoroacetic acid, acetic acid, formic acid, methanesulfonic acid, toluenesulfonic acid, maleic acid, fumaric acid and camphorsulfonic acid. Salts prepared with bases include ammonium salts, alkali metal salts, e.g. sodium and potassium salts, and alkali earth salts, e.g. calcium and magnesium salts. Acetate, hydrochloride, and trifluoroacetate salts are preferred. The salts may be formed by conventional means, as by reacting the free acid or base forms of the product with one or more equivalents of the appropriate base or acid in a solvent or medium in which the salt is insoluble, or in a solvent such as water which is then removed in vacuo or by freeze-drying or by exchanging the ions of an existing salt for another ion on a suitable ion exchange resin.

The compounds described above are useful in view of their pharmacological properties. In particular, the compounds of the invention possess activity as agents to slow gastric emptying, as evidenced by the ability to reduce post-prandial glucose levels in mammals.

As described in Example 1, the effects of amylin on oral glucose tolerance tests in dogs was evaluated. Surprisingly, amylin, which has-been previously described as a hyperglycemic agent (i.e., one causing elevated glucose), was found instead to decrease-post-prandial plasma glucose levels in these test animals. Amylin, at all dose rates tested, reduced both the rate of rise in plasma glucose as well as the peak plasma glucose in the oral glucose tolerance test.

Example 2 describes the effects of the amylin agonist, AC-0137, on post-prandial plasma glucose levels in human clinical trials. With both bolus and continuous intravenous infusion of AC-0137, a dose-dependent reduction in post-prandial hyperglycemia was observed in subjects with juvenile-onset diabetes mellitus.

Example 3 describes the effect of continuous infusion of AC-0137 (tripro-amylin) on plasma glucose levels after Sustacal® meal and after IV glucose load. With IV glucose load, plasma glucose levels in subjects treated with 50 µg/hr AC-0137 were not significantly different from placebo-treated subjects. However, in subjects given a Sustacal meal treated with 25 µg/hr or 50 µg/hr IV infusion of AC-0137, plasma glucose levels were reduced in AC-0137-treated subjects compared with placebo. AC-0137 reduced post-prandial plasma glucose concentrations in insulin dependent diabetic patients after oral nutrients, but had no measurable effect on plasma glucose concentrations following the administration of an intravenous glucose load.

As described in Example 4, in a 14-day double-blind, placebo-controlled clinical study, patients with juvenile-onset diabetes who continued their usual insulin therapy and self-injected tripro-amylin (AC-0137) three times daily had lower average blood glucose levels after a test meal than did patients who received insulin and placebo. After 14 days, a statistically significant (P=0.02) glucose smoothing effect (measured as area under the glucose curve) was observed at the 30 micrograms, peak tripro-amylin plasma concentrations were within the range of amylin found in the blood of non-diabetic individuals. The tripro-amylin induced reductions in AUC accompanied average reductions of 45 mg/dl to 60 mg/dl in the peak blood glucose concentrations of the subjects.

As described in Example 5 gastric emptying was measured in normal and insulin-treated spontaneously diabetic BB rats using the retention of an a caloric methylcellulose gel containing Phenol Red delivered by gavage. Dye content in stomachs removed after sacrifice 20 min later was determined spectroscopically, and was compared to that in rats sacrificed immediately after gavage to assess emptying. Diabetic rats had a markedly greater gastric emptying (90.3±1.7% passed) compared to normal Harlan Sprague Dawley rats (49.1±4.7% passed; P<0.001) and non-diabetic BB rats (61.1±9.2% passed; P<0.001). The pancreatic β-cell peptide, amylin, which is deficient in IDDM, dose-dependently inhibited gastric emptying in both normal and diabetic rats. The $ED_{50}$ of the response in both normal and diabetic rats was ~1 µg, a dose that resulted in a peak amylin concentration of 76 pM 20 minutes after injection. These concentrations are within the range observed in vivo. These results support the determination that amylin participates in the physiological control of nutrient entry into the duodenum.

As described in Example 6, the uptake of ingested labelled glucose load was measured in conscious, fasted, corpulent LA/N rats. Preinjection with the amylin receptor antagonist, AC-0187, accelerated the appearance of glucose-derived tritium in the plasma. Additionally, preinjection with amylin antagonist resulted in a greater rise in plasma glucose 15 minutes after gavage and in an earlier decline of plasma glucose levels. These data are consistent with the amylin antagonist AC-0187 having counteracted an effect of endogenously secreted amylin, thereby accelerating gastric emptying.

In additional studies in anesthetized rats, it was found that amylin does not affect glucose absorption into the blood from the small intestine. In those experiments, anesthetized rats were continuously infused with rat amylin (0.35 nm/kg/min) or saline, in the case of control animals, for 3 hours. After one hour of amylin infusion, a bolus of glucose (1g/kg) was infused either into the stomach or the duodenum through a tube inserted through the esophagus. Because-the studies involved anesthetized rather than conscious rats, they are not considered in analyzing gastric motility, e.g., rate of emptying of stomach contents into the duodenum. However, the studies indicate that absorption of glucose from the duodenum into the blood was not delayed by amylin. A different preparation was used to more directly address whether amylin affected the transit of glucose from the small bowel lumen into the blood. In anesthetized rats, a segment of small bowel, still connected to the animal via its blood supply, was exteriorized and cannulae inserted so that the small bowel could be perfused with glucosed solutions of controlled composition. The animals were cannulated also via an artery (for blood sampling) and via a vein (for infusion of amylin, insulin and glucose). The lumen was perfused with a tritium-labelled glucose solution. The passage of glucose from the lumen of the gut into the rat was measured by the appearance of the tritium label in the plasma. The supposition that such appearance of tritium in the plasma was indeed measuring glucose uptake from the gut was tested by administration of the glucose transport blocker, phloridzin. Phloridzin largely prevented the transit of label from the gut lumen into the plasma. To ensure that the glucose gradient between the gut lumen and plasma remained constant, during amylin infusions, plasma glucose was "clamped" by an infusion of glucose that was varied in response to changes in.-plasma glucose. In this preparation, intravenous amylin infusions had no effect upon the rate at which labelled glucose presented to the small bowel entered the plasma. These results show that the decreased blood glucose observed in amylin-treated subjects in the studies described above are not likely due to a decrease in absorption from the small intestine, but rather to a decreased rate of transfer of stomach contents to the duodenum. i.e., due to delayed gastric emptying.

Compositions useful in the invention may conveniently be provided in the form of formulations suitable for parenteral (including intravenous, intramuscular and subcutaneous) or nasal or oral administration. In some cases, it will be convenient to provide an amylin agonist and another anti-emptying agent, such as glucagon, in a single composition or solution for administration together. In other cases, it may be more advantageous to administer another anti-emptying agent separately from said amylin or amylin agonist analogue. A suitable administration format may best be determined by a medical practitioner for each patient individually. Suitable pharmaceutically acceptable carriers and their formulation are described in standard formulation treatises, e.g., *Remington's Pharmaceutical Sciences* by E. W. Martin. See also Wang, Y. J. and Hanson, M. A. "Parenteral Formulations of Proteins and Peptides: Stability and Stabilizers," *Journal of Parenteral Science and Technology*, Technical Report No. 10, Supp. 42:2S (1988). Suitable formulations including hypoglycemic agents such as sulfonylureas are known in the art.

Compounds useful in the invention can be provided as parenteral compositions for injection or infusion. They can, for example, be suspended in an inert oil, suitably a vegetable oil such as sesame, peanut, olive oil, or other acceptable carrier. Preferably, they are suspended in an aqueous carrier, for example, in an isotonic buffer solution at a pH of about 5.6 to 7.4. These compositions may be sterilized by conventional sterilization techniques, or may be sterile filtered. The compositions may contain pharmaceutically acceptable auxiliary substances as required to approximate physiological conditions, such as pH buffering agents. Useful buffers include for example, sodium acetate/acetic acid buffers. A form of repository or "depot" slow release preparation may be used so that therapeutically effective amounts of the preparation are delivered into the bloodstream over many hours or days following transdermal injection or delivery.

The desired isotonicity may be accomplished using sodium chloride or other pharmaceutically acceptable agents such as dextrose, boric acid, sodium tartrate, propylene glycol, polyols (such as mannitol and sorbitol), or other inorganic or organic solutes. Sodium chloride is preferred particularly for buffers containing sodium ions.

If desired, solutions of the above compositions may be thickened with a thickening agent such as methyl cellulose. They may be prepared in emulsified form, either water in oil or oil in water. Any of a wide variety of pharmaceutically acceptable emulsifying agents may be employed including, for example, acacia powder, a non-ionic surfactant (such as a Tween), or an ionic surfactant (such as alkali polyether alcohol sulfates or sulfonates, e.g., a Triton).

Compositions useful in the invention are prepared by mixing the ingredients following generally accepted procedures. For example, the selected components may be simply mixed in a blender or other standard device to produce a concentrated mixture which may then be adjusted to the final concentration and viscosity by the addition of water or thickening agent and possibly a buffer to control pH or an additional solute to control tonicity.

For use by the physician, the compositions will be provided in dosage unit form containing an amount of an amylin or amylin agonist, for example, an amylin agonist analogue compound with or without another antiemptying agent which will be effective in one or multiple doses to control blood sugar at the selected level. Therapeutically:effective amounts of an amylin or amylin agonist, such as an amylin agonist analogue, for use in the control of gastric emptying and in conditions-in which gastric emptying is beneficially slowed or regulated are those that decrease post-prandial blood glucose levels, preferably to no more than about 8 or 9 mM or such that blood glucose levels are reduced as desired. In diabetic or glucose intolerant individuals, plasma glucose levels are higher than in normal individuals. In such individuals, beneficial reduction or "smoothing" of post-prandial blood glucose levels, may be obtained. As will be recognized by those in the field, an effective amount of therapeutic agent will vary with many factors including the age and weight of the patient, the patient's physical condition, the blood sugar level or decrease in amylin action to be obtained, and other factors.

Such pharmaceutical compositions are useful in causing gastric hypomotility in a subject and may be used as well in other disorders where gastric motility is beneficially reduced.

The effective daily anti-emptying dose of the compounds including $^{18}$Arg$^{25,28}$Pro-h-amylin, des-$^{1}$Lys$^{18}$Arg$^{25,28}$Pro-h-amylin, $^{18}$Arg$^{25,28,29}$Pro-h-amylin, des-$^{1}$Lys$^{18}$Arg-$^{25,28,}$ $_{29}$Pro-h-amylin, $^{25,28,29}$Pro-h-amylin, des-$^{1}$Lys$^{25,28,29}$Pro-h-amylin, and $^{25}$Pro$^{26}$Val$^{25,28}$Pro-h-amylin, will typically be in the range of 0.01 or 0.03 to about 5 mg/day, preferably about 0.01 or 0.5 to 2 mg/day and more preferably about 0.01 or 0.1 to 1 mg/day, for a 70 kg patient, administered in a single or divided doses. The exact dose to be administered is determined by the attending clinician and is dependent upon where the particular compound lies within the above quoted range, as well as upon the age, weight and condition of the individual. Administration should begin at the first sign of symptoms or shortly after diagnosis of diabetes mellitus. Administration may be by injection, preferably subcutaneous or intramuscular. Orally active compounds may be taken orally, however dosages should be increased 5–10 fold.

Generally, in treating or preventing elevated, inappropriate, or undesired post-prandial blood glucose levels, the compounds of this invention may be administered to patients in need of such treatment in a dosage ranges similar to those given above, however, the compounds are administered more frequently, for example, one, two, or three times a day.

Amylin antagonists, useful in treating gastric hypomotility, may be administered in a dosage of from 0.1 to 30 mg/day, preferably 0.3 to 10 mg/day and preferably 0.1 to 3 mg/day. Administration may be by, for example, subcutaneous or intramuscular injection. Orally active compounds may be taken orally, however dosages should be increased 5–10 fold.

To assist in understanding the present invention, the following Examples are included which describes the results of a series of experiments. The experiments relating to this invention should not, of course, be construed as specifically limiting the invention and such variations of the invention, now known or later developed, which would be within the purview of one skilled in the art are considered to fall within the scope of the invention as described herein and hereinafter claimed.

EXAMPLE 1

Previous studies have demonstrated that intravenous amylin injections into fasted and fed rats under glucose tolerance test conditions can decrease the plasma glucose decline and increase plasma lactate in a dose-dependent manner. Insulin responses are also significantly depressed by amylin infusions in fasted animals.

However, the following studies and experiments showed that amylin infusion decreased the plasma glucose levels in dogs in response to an oral glucose level. The purposes of these studies were: (1) to evaluate the changes in plasma glucose, lactate and insulin in response to an oral glucose load: (2) to evaluate the effects of intravenously administered amylin on these variables; and, (3) to evaluate the efficacy of the amylin antagonist AC-0253 (acetyl-$^{11,18}$Arg, $^{30}$Arg, $^{32}$Tyr-$^{9-32}$ calcitonin (salmon)) to reverse any amylin-induced changes in blood plasma glucose.

Mongrel dogs (9 males, 12–17 kg wt. range) were used for this study. All animals were fasted overnight prior to each study. Each animal served as its own control for all protocols. Animals were equilibrated for 30–60 minutes prior to the start of each protocol.

At t=–30, vehicle, or amylin ± AC-0253 was begun. Amylin dose rates were 50, 100 and 300 pmol/kg/min. Dose rates of AC-0253 were 500 and 1500 pmol/kg/min. 25% glucose (1 gm/kg) was administered by mouth at t=0 minutes. Amylin ± AC-0253 was discontinued at t=120 minutes. Samples for insulin, glucose and lactate were obtained at 15 minute intervals from t=–45 to t=180 minutes. Samples for rat amylin and AC-0253 were taken at t=60 and 120 minutes.

In normal dogs, the peak in plasma glucose occurs between 30–45 minutes after an oral glucose load in conscious dogs. Although there was considerable inter-dog variability, the patterns of response were repeatable for each individual dog. Amylin, at all dose rates tested, reduced both the rate of rise in plasma glucose as well as the peak plasma glucose. During the amylin infusion, the plasma glucose-appeared to reach a plateau, at a plasma glucose significantly lower than in the control experiments, at 30 to 45 minutes and began to increase again after the amylin infusion was terminated. There were no differences in the changes in plasma glucose between amylin doses rates of 50, 100 and 300 pmol/kg/min.

An amylin dose rate of 50 pmol/kg/min was selected for the experiments performed-to evaluate the efficacy of AC-0253 to reverse amylin-induced changes in the plasma glucose. AC-0253 at up to 1500 pmol/kg/min does not completely reverse the effects of amylin (50 pmol/kg/min). AC-0253 alone has no effect on the changes in plasma glucose. The effects of amylin and AC-0253 on plasma lactate were unremarkable.

EXAMPLE 2

Twenty-four male subjects with insulin-dependent diabetes mellitus participated in a clinical study of the amylin agonist AC-0137. Each subject was randomly assigned to one of four treatment groups receiving placebo, 30, 100 or 300 µg AC-0137. Subjects in each dose group underwent a two period crossover to examine intravenous (IV) bolus versus IV infusion of drug. Each period consisted of a three-day confinement to the study unit. On each occasion, the initial day of confinement was allowed for acclimatization to the study unit. The second and third days constituted an imbedded crossover of placebo versus active medication. For example, subjects randomized to receive IV bolus first were further assigned to receive AC-0137 IV bolus on one day and placebo IV bolus on the other day (or the opposite order of bolus placebo followed by bolus AC-0137). After two weeks, the subjects were re-admitted to receive the same dose of: AC-0137 via the opposite means of administration, i.e., IV infusion. An imbedded cross-over design for the administration of drug and placebo on Days 2 and 3 of this admission was employed in a manner similar to that used during the first admission. The six subjects assigned to the placebo group received placebo on each of the study days.

On study days, intravenous catheters were inserted at least 30 minutes prior to the start of the study. 15 minutes before dosing, the subjects took their usual insulin dose via subcutaneous injection. At time 0, subjects either received an IV bolus injection of the assigned dose of AC-0137 or placebo over two minutes or a continuous infusion of AC-0137 or placebo was begun and continued for two hours. The infusion rate was designed to administer the assigned amount of drug over the two hour period. Thirty minutes later, the subjects ingested their normal breakfasts. Blood samples were taken between –30 and 300 minutes for the measurement of plasma AC-0137 levels and plasma glucose levels.

Plasma drug levels followed the expected course peaking early after bolus injection and then disappearing from the plasma compartment with apparent first-order kinetics. In contrast, the continuous infusions lead to levels which approximated steady-state within 30-minutes and were then maintained at that level throughout the remainder of the infusion. Upon cessation of the infusion, the plasma levels decayed in a manner similar to that observed with IV bolus administration.

The plasma glucose profiles revealed some unexpected and interesting results. As can be appreciated from the subjects who received placebo on each occasion, plasma glucose levels were elevated above baseline by 60–90 minutes and remained elevated at least until 240 minutes. IV bolus administration of AC-0137 resulted in no apparent change in glucose levels following the 30 µg dose. With the 100 µg bolus, the post-prandial rise in glucose was clearly delayed and less pronounced. Following the 300 µg bolus, the post-prandial rise in glucose levels was essentially eliminated.

With continuous, intravenous infusion, a dose-dependent reduction in post-prandial hyperglycemia was observed. The data from the 15 µg/hr infusion is highly suggestive of an effect, and as the infusion rate increased to 50 and 150 µg/hr, the reduction of the post-prandial rise in glucose levels is striking. Similar trends are apparent in the studies employing bolus administration of drug.

EXAMPLE 3

A single blind, placebo controlled, two period, cross-over study with a minimum 15 hour washout between treatments was undertaken to further demonstrate the effect-of tripro-amylin (AC-0137) in reducing post-prandial hyperglycemia and to confirm that the reduction in post-prandial hyperglycemia is primarily a gastrointestinal effect. Twenty-seven subjects with insulin-dependent diabetes mellitus were allocated into a combination of two dose level groups and two types of tolerance tests. Subjects received treatment with a continuous micro-infusion pump of AC-0137 and placebo, in accordance with the cross-over design. The subjects were divided into three groups with nine subjects each, as follows: Group A received Sustacal® meals and an AC-0137 dose of 25 µg/hr. Group B received Sustacal® meals and an AC-0137 dose of 50 µg/hr. Group C received intravenous glucose load and an AC-0137 dose of 50 µg/hr.

Subjects remained in the clinic for three days. On the first day of confinement, the subjects were acclimatized to the clinic. On Days 2 and 3 the subjects completed a two-period cross over design of AC-0137 versus placebo. In addition, subjects received either a Sustacal® meal or iv glucose tolerance test, as determined by the group assignment.

During the first day, the subject's usual insulin and caloric intake was stabilized and each subject then followed this insulin and dietary regimen throughout confinement in the clinic.

At approximately, 0700h (T=0), the continuous infusion of study medication was initiated. At T=30 minutes, the subjects administered their usual AM dose of insulin. At T=60 minutes, subjects were given a standardized Sustacal® meal containing 355 calories to drink or an iv glucose load of 300 mg/kg, administered as an i.v. infusion of $D_{50}W$ over five minutes using an infusion pump. The type of tolerance test was determined according to the randomization schedule. Blood samples were taken at regular intervals for measurement of glucose, lactate and insulin and for the determination of AC-0137 plasma concentrations. Study drug administration was discontinued at t=300 minutes.

On the morning of the third day, iv lines were again placed in a similar manner as on Day 2. Subjects administered their usual pre-breakfast dose of insulin as on Day 2. Subjects received placebo or study medication in crossover fashion using the same iv route and regimen as the previous day (i.e. subjects who received AC-0137 infusion on the second day received placebo infusion on the third day). An identical standardized Sustacal meal tolerance or iv glucose load as they received on Day 2 was again administered. At the end of the sampling period the iv lines were withdrawn.

Figure 10A:
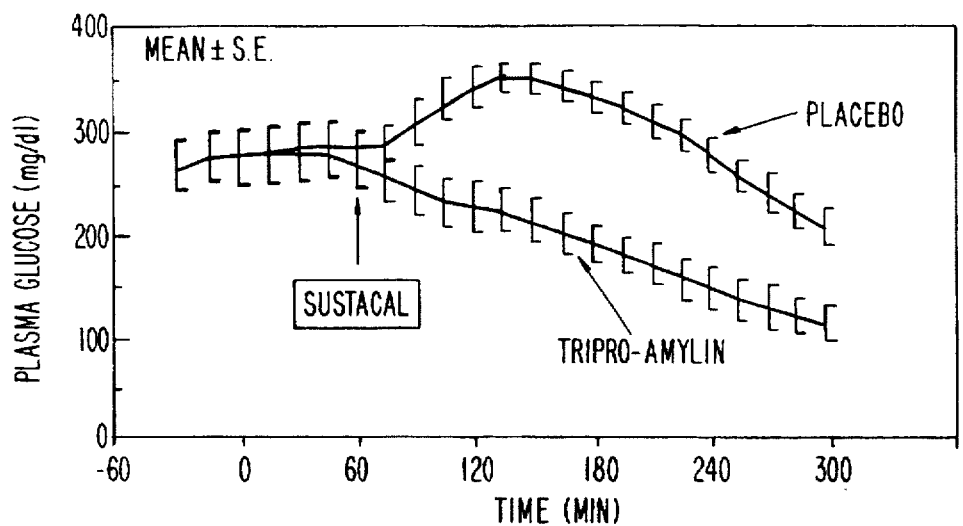
FIGS. 10A–C show plasma glucose (mg/dl), plasma tripro-amylin (pM), and plasma free insulin concentrations (µU/ml) from the time 60 minutes prior to initiation of an IV infusion of 50 µg/hr tripro-amylin. An IV glucose load (300 mg/kg) was given at 60 minutes after start of tripro-amylin infusion.
Figure 10B:
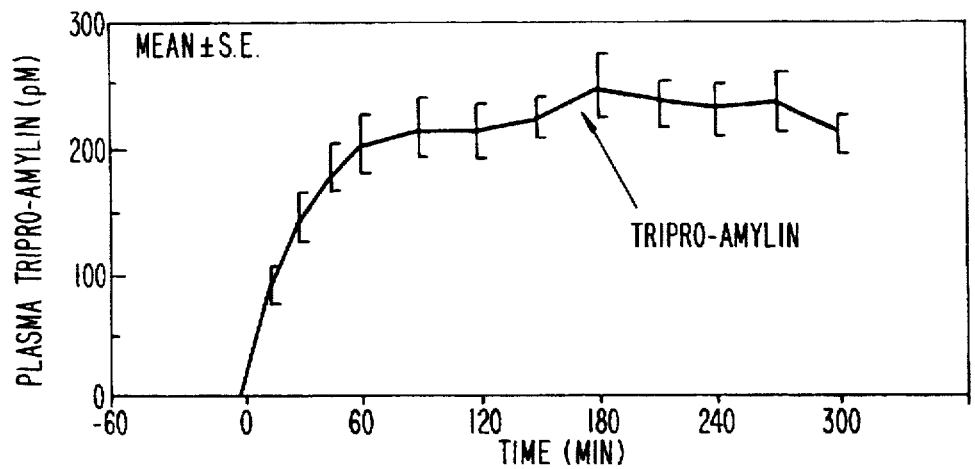
Figure 10C:
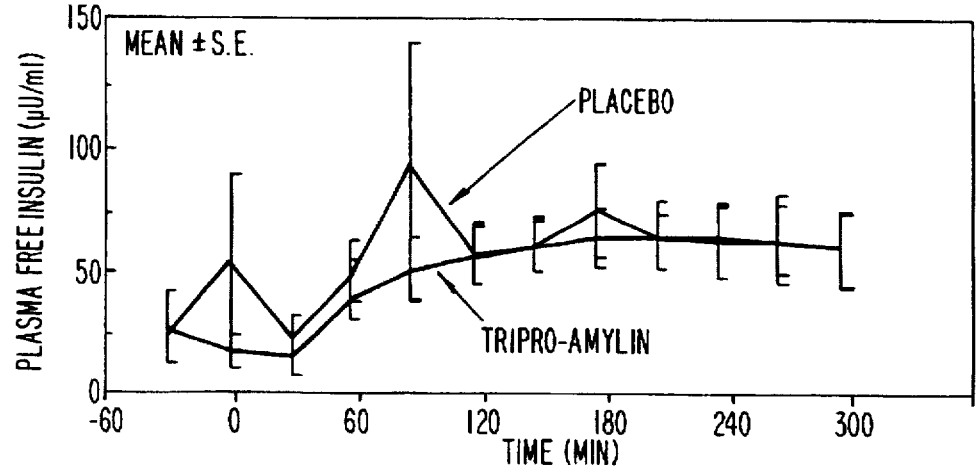

As shown in FIGS. 10A–C IV glucose load, plasma glucose levels in subjects treated with 50 µg/hr AC-0137 were not significantly different from placebo-treated subjects. These differences in post-injection of glucose concentrations were statistically significant-when-area under the glucose curves, corrected for baseline values were compared (P=0.0015). Thus, the observation of reduced post-prandial hyperglycemia during AC-0137 administration was confirmed employing a standardized meal in the presence of significantly lower mean plasma AC-0137 concentrations than those used previously.

Figure 1:
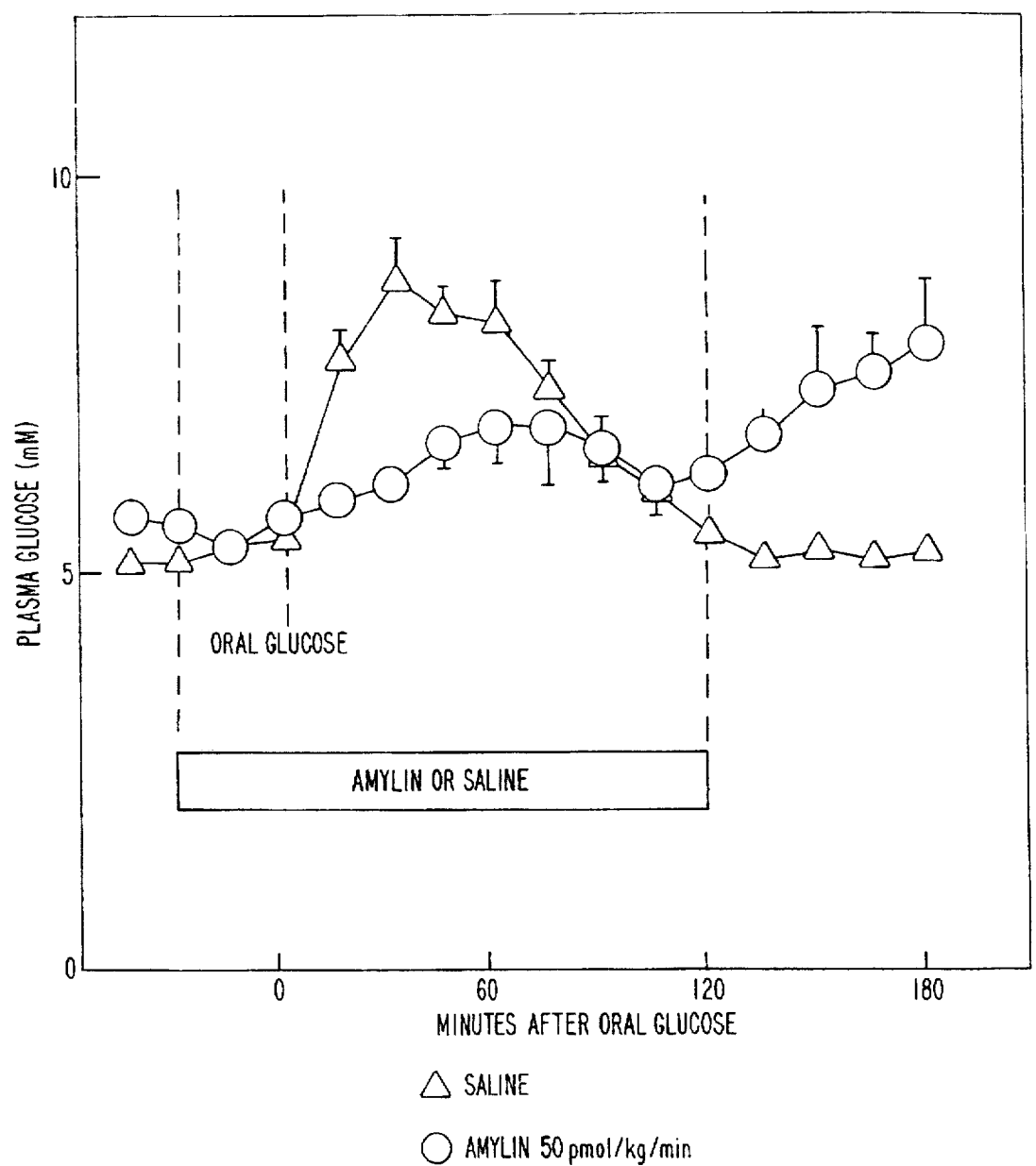
FIG. 1 shows the effect of amylin on plasma glucose levels in dogs following an oral glucose load, compared to control.
Figure 2:
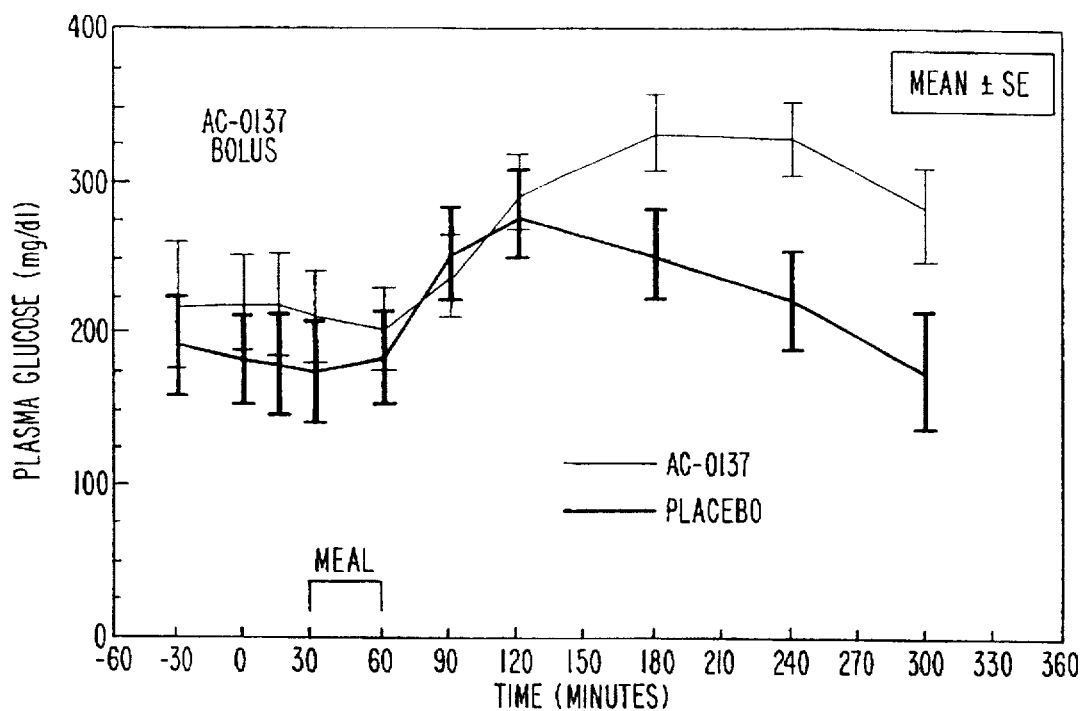
FIG. 2 shows the post-prandial glucose profiles of human clinical volunteers administered placebo or an IV bolus of 30 µg AC-0137.
Figure 3:
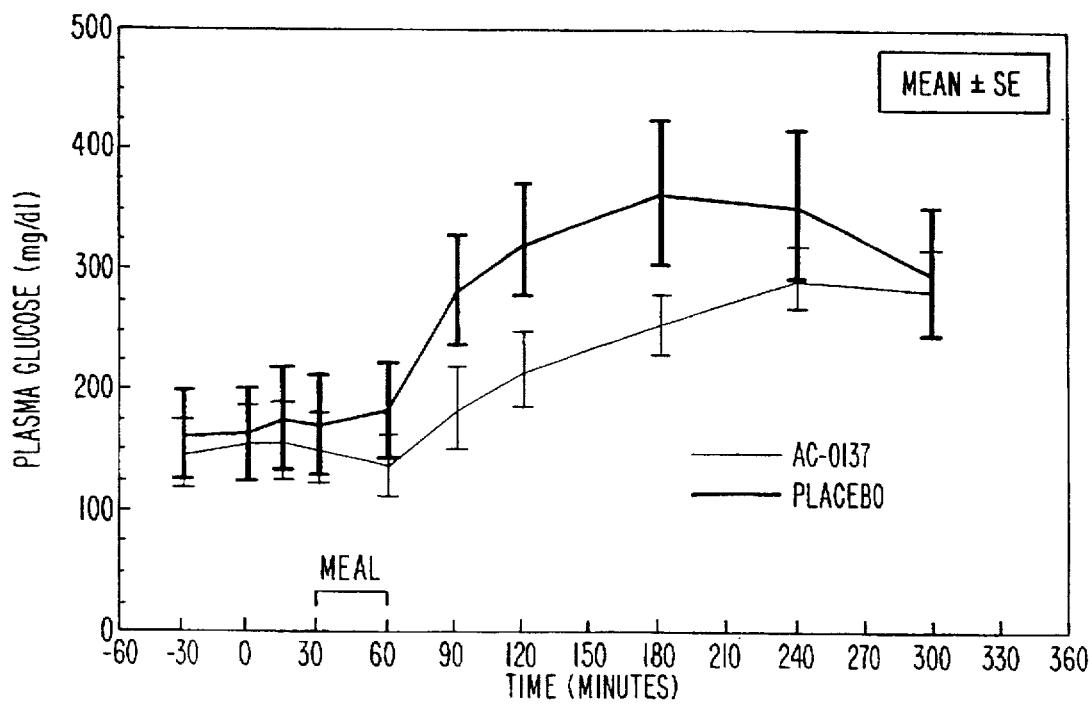
FIG. 3 shows the post-prandial glucose profiles of human clinical volunteers administered placebo or an IV bolus of 100 µg AC-0137.
Figure 4:
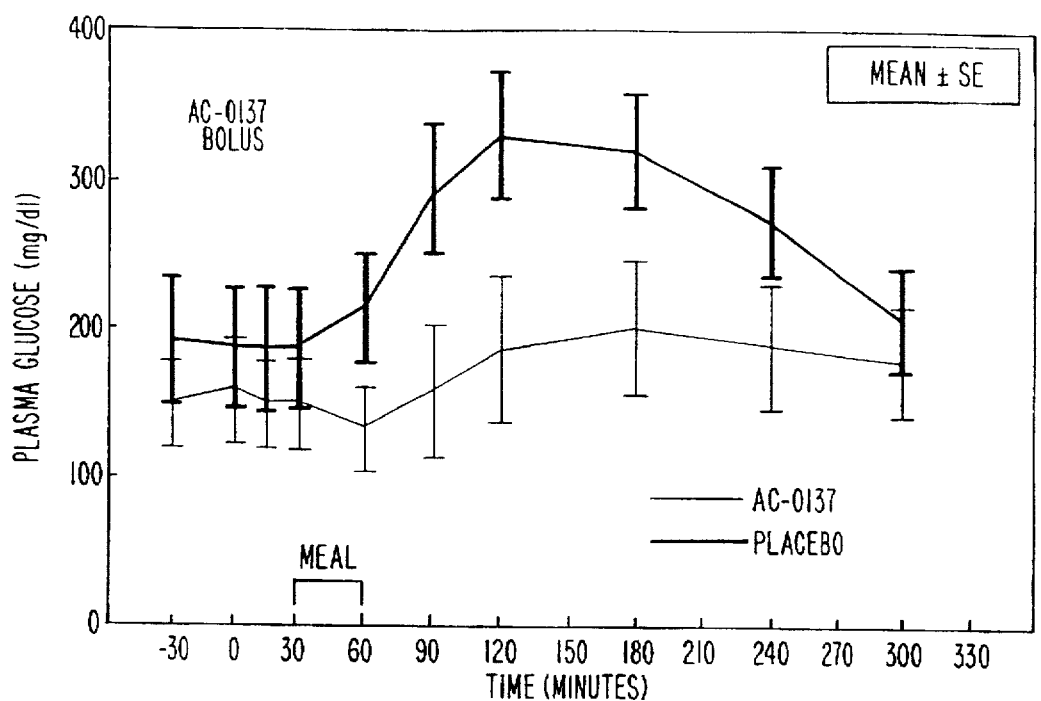
FIG. 4 shows the post-prandial glucose profiles of human clinical volunteers administered placebo or an IV bolus of 300 µg AC-0137.
Figure 5:
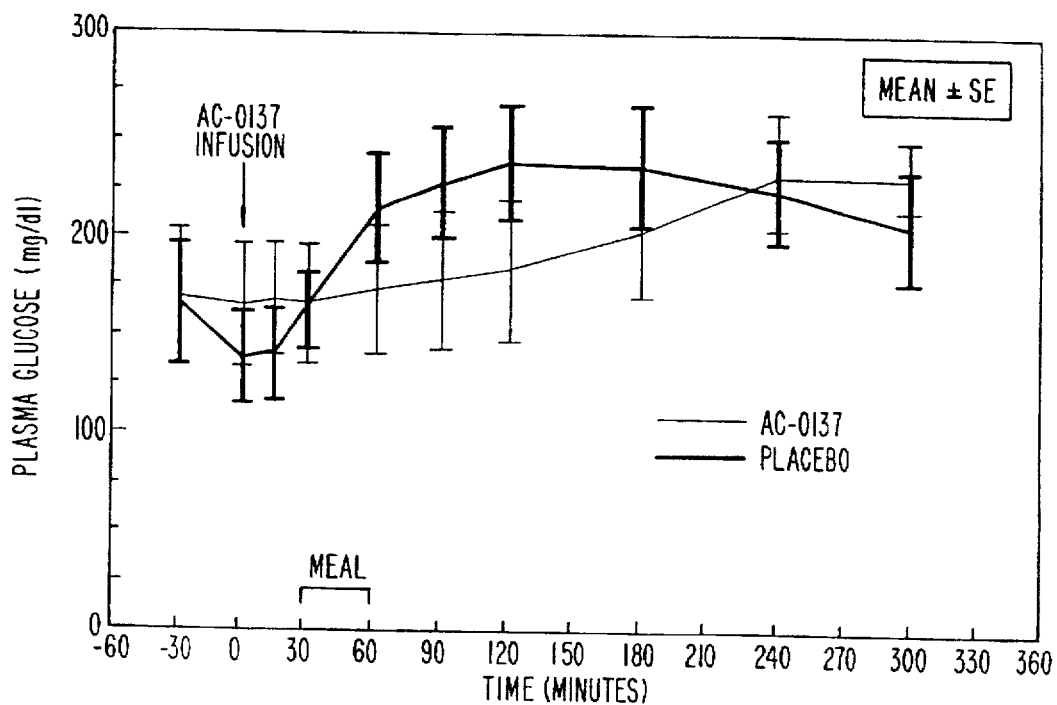
FIG. 5 shows the post-prandial glucose profiles of human clinical volunteers administered placebo or a 2-hour IV infusion of AC-0137, at 15 µg/hour.
Figure 6:
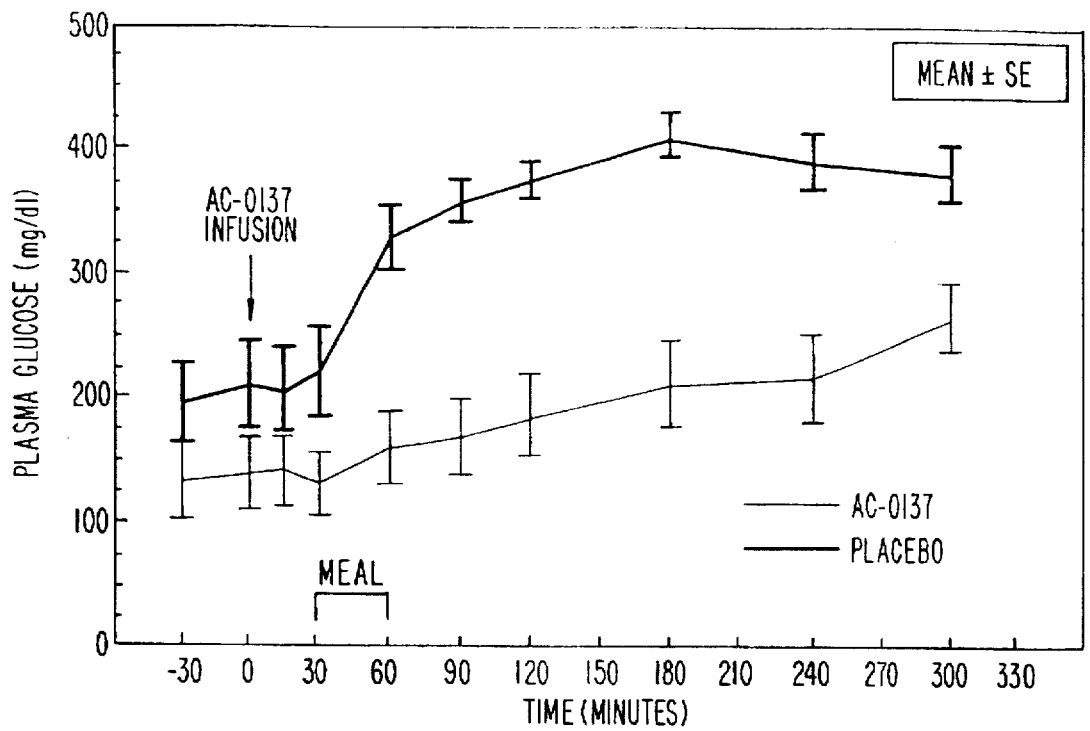
FIG. 6 shows the post-prandial glucose profiles of human clinical volunteers administered placebo or a 2-hour IV infusion of AC-0137, at 50 µg/hour.
Figure 7:
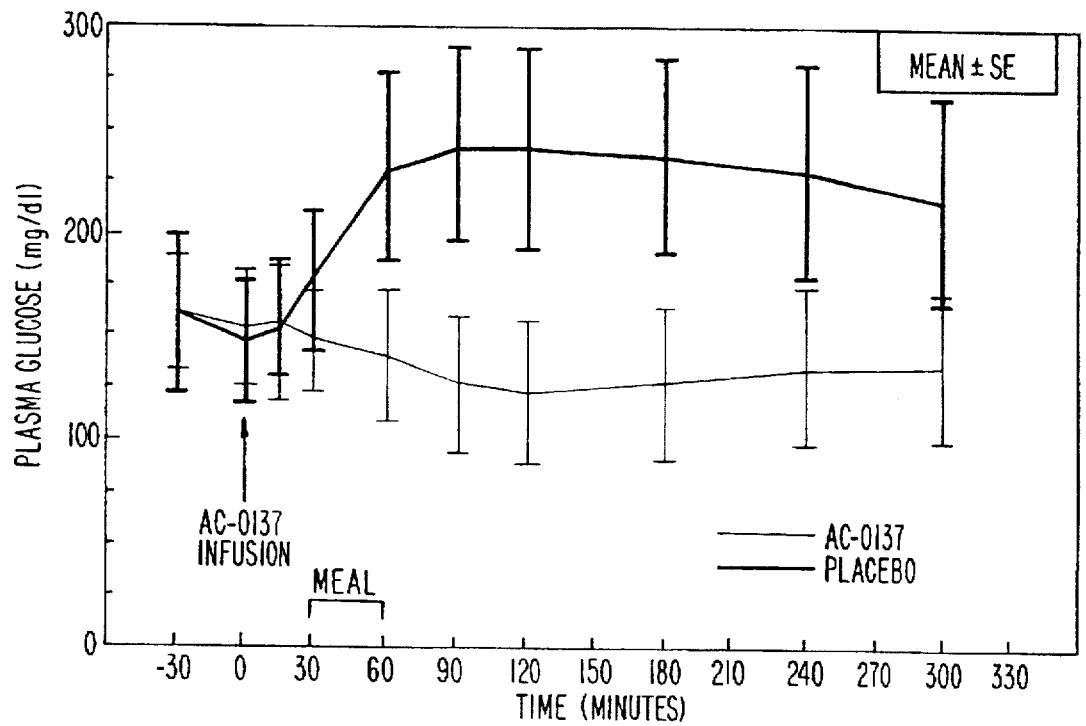
FIG. 7 shows the post-prandial glucose profiles of human clinical volunteers administered placebo or a 2-hour IV infusion of AC-0137, at 150 µg/hour.
Figure 8A:
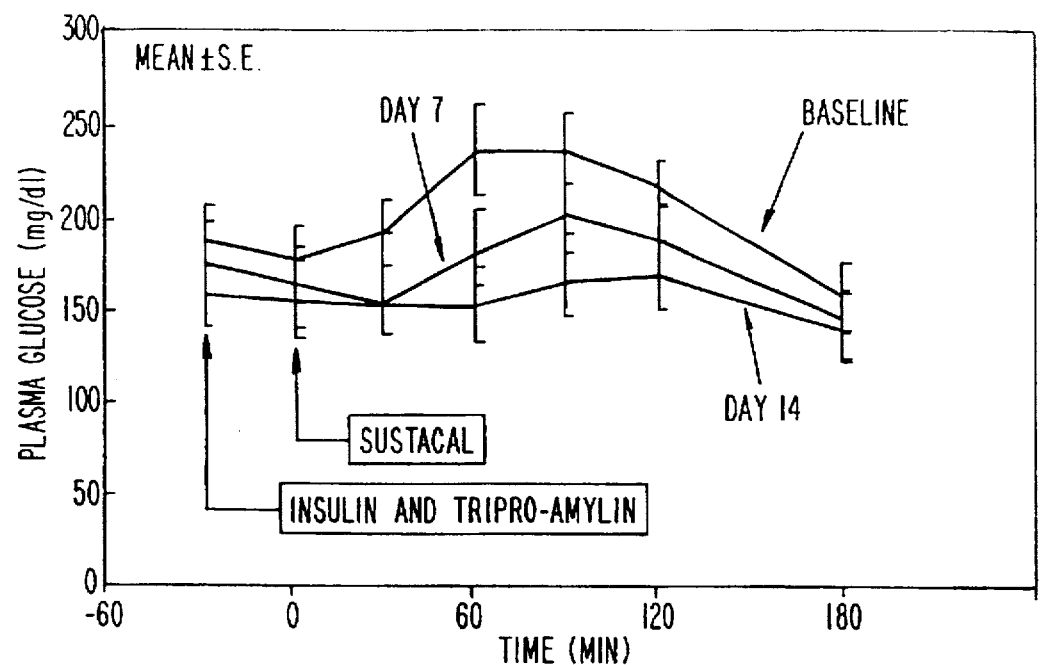
FIGS. 8A and 8B show plasma glucose (mg/dl), plasma tripro-amylin (pM), and plasma free insulin concentrations (µU/ml) from the time 60 minutes prior to initiation of an IV infusion of 25 µg/hr tripro-amylin Sustacal® meal was given at 60 minutes after start of tripro-amylin infusion.
Figure 8B:
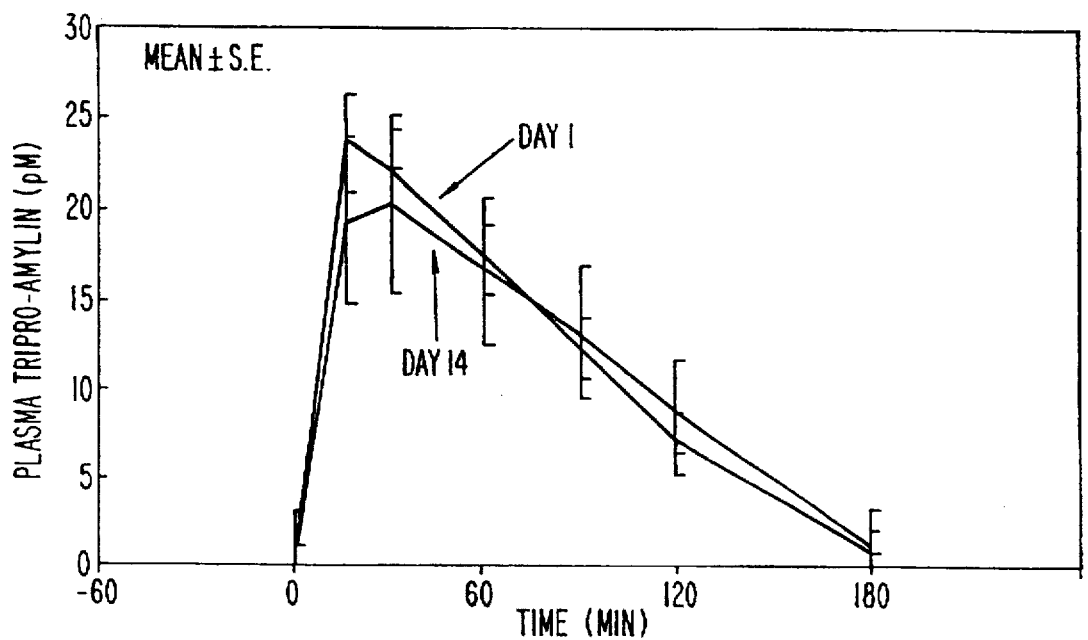
Figure 9A:
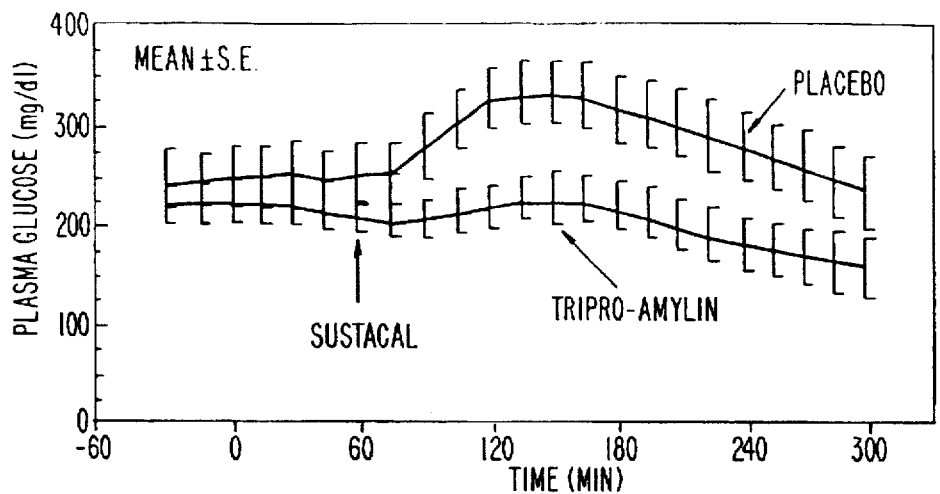
FIGS. 9A–C show plasma glucose (mg/dl), plasma tripro-amylin (pM), and plasma free insulin concentrations (U/ml) from the time 60 minutes prior to initiation of an IV infusion of 50 gg/hr tripro-amylin. Sustacal® meal was given at 60 minutes after start of tripro-amylin infusion.
Figure 9B:
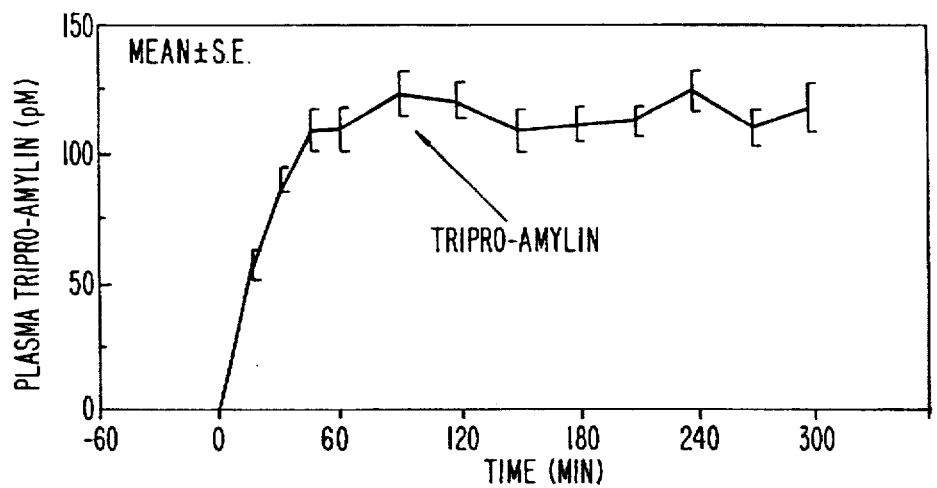
Figure 9C:
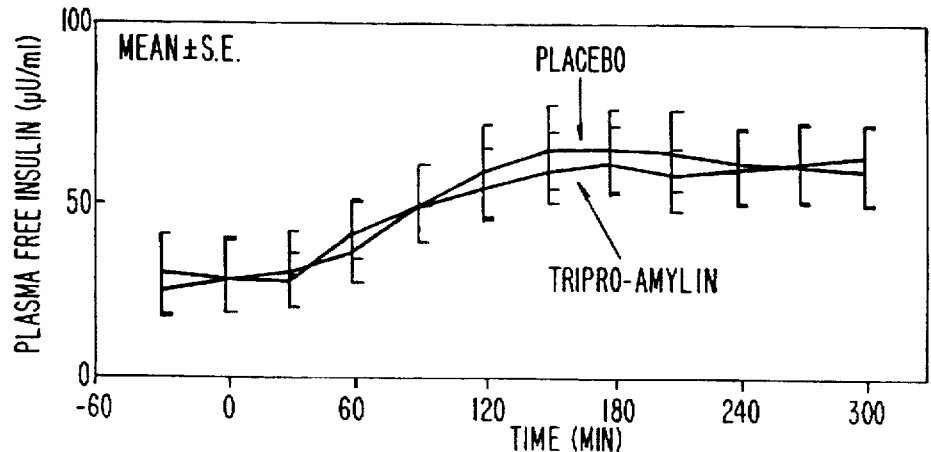

However, as shown in FIGS. 8A and B and 9A and B, in subjects given a Sustacal® meal treated with 25 µg/hr or 50 µg/hr IV infusion of AC-0137, plasma glucose levels were reduced in AC-0137-treated subjects compared with placebo.

AC-0137, at tolerable pharmacological doses, reduced post-prandial plasma glucose concentrations in insulin-dependent diabetic patients after oral nutrients, but had no measurable effect on plasma glucose concentrations following the administration of an intravenous glucose load. These results are consistent with the idea that AC-0137 modifies the uptake of oral nutrients from the gut, and indicate that an alteration in the rate of gastric emptying accounts for at least a portion of this effect.

EXAMPLE 4

A randomized, double-blind, placebo-controlled, parallel group was undertaken to determine the effect of tripro-amylin (AC-0137) on plasma glucose levels following ingestion of a Sustacal® standardized meal (Mead-Johnson). 72 subjects with insulin-dependent diabetes mellitus participated in a 14-day clinical trial. Each subject was randomly assigned to one of four treatment groups, receiving placebo, 30, 100 or 300 µg tripro-amylin by subcutaneous injection three times a day for 14 days. The subjects also remained on their usual insulin regimen throughout the study. On days 1 (baseline), 7 and 14, standardized meal tolerance tests were performed.

For the standardized meal tolerance tests, subjects were given a Sustacal® liquid meal (360 ml containing 360 calories) at 0800 h. Subjects abstained from food or drink (except for water) from 2200 h the night before. Subjects did not administer their usual morning dose of insulin until 30 minutes before the Sustacal® meal. For a baseline test, on day 1, tripro-amylin (or placebo) was not administered until after completion of the test. On days 7 and 14, tripro-amylin (or placebo) was administered in a separate injection at the same time as the usual morning insulin dose. Samples for determination of serum glucose levels were drawn at −30, 0, 30, 60, 120 and 180 minutes relative to the start of the challenge. Time zero was considered to be the time when the subject began to drink the Sustacal® meal.

Figure 11A:
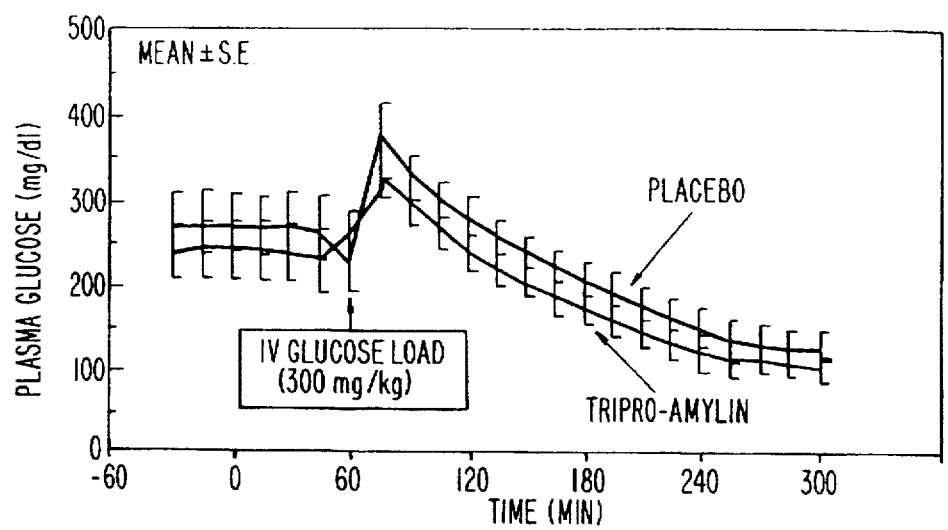
FIGS. 11A–C show the post-Sustacal® meal glucose profiles for baseline (day 1), day 7 and day 14 Sustacal® meal tolerance tests of human clinical volunteers administered 30 µg tripro-amylin (AC-0137) three times a day before meals over a 14-day period.
Figure 11B:
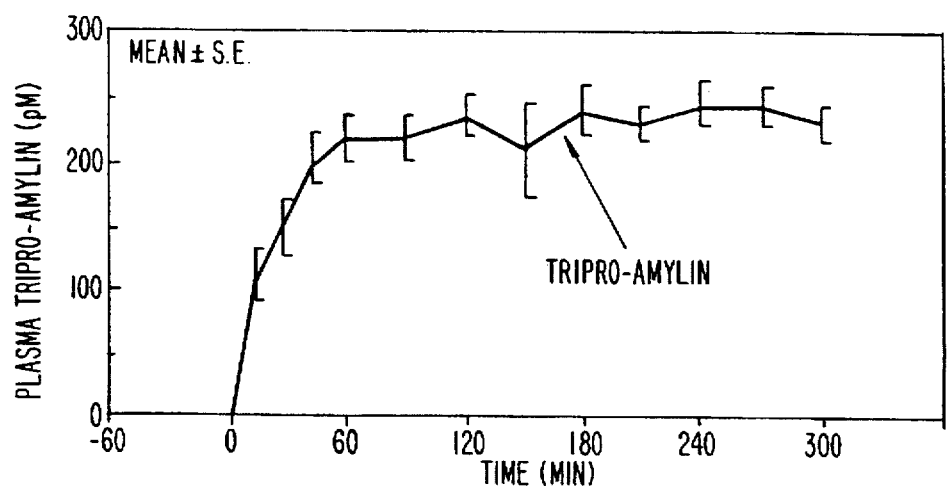
Figure 11C:
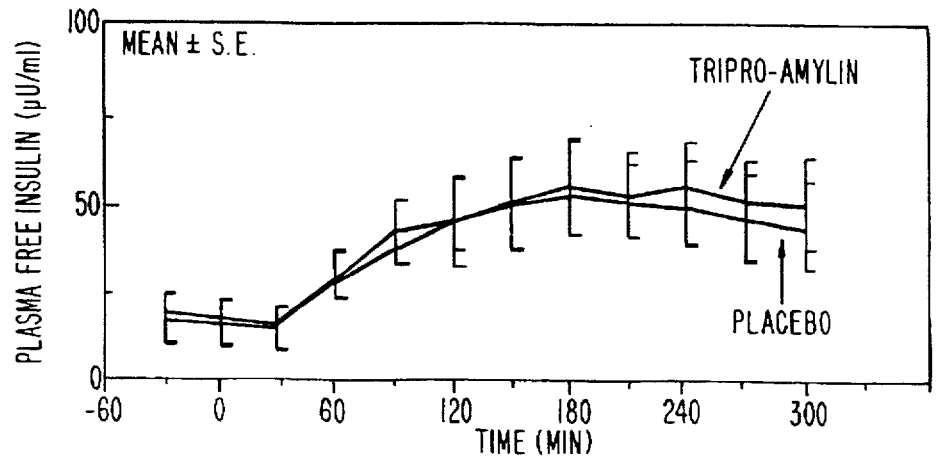
Figure 12A:
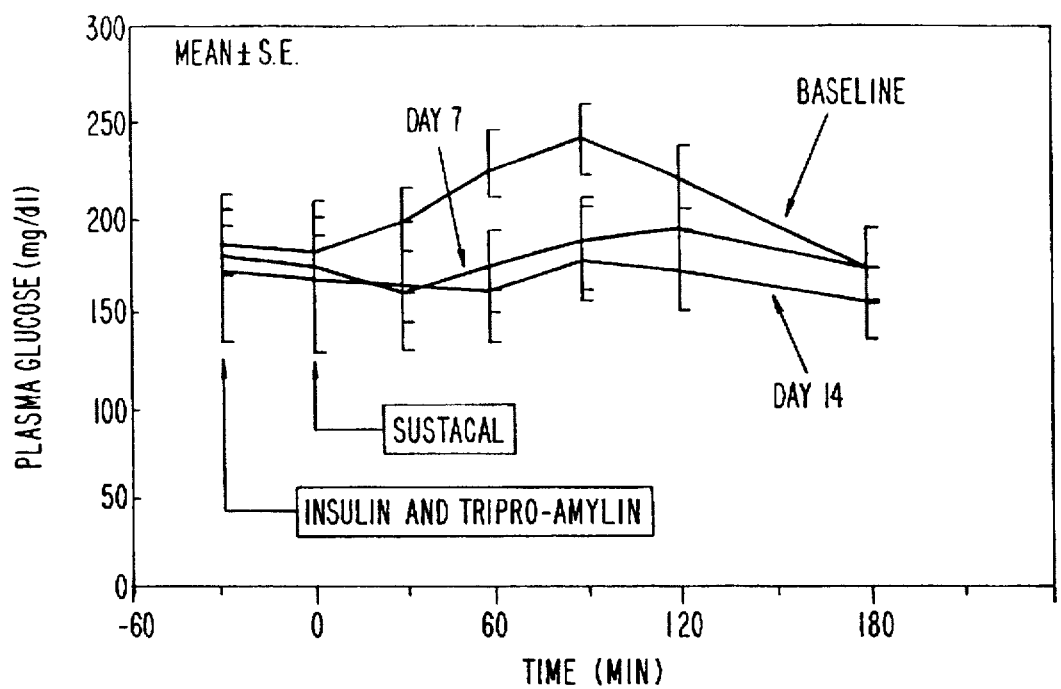
FIGS. 12A and B show the post-Sustacal® meal glucose profiles for baseline (day 1), day 7 and day 14 Sustacal® meal tolerance tests of human clinical volunteers administered 100 µg tripro-amylin (AC-0137) three times a day before meals over a 14-day period.
Figure 12B:
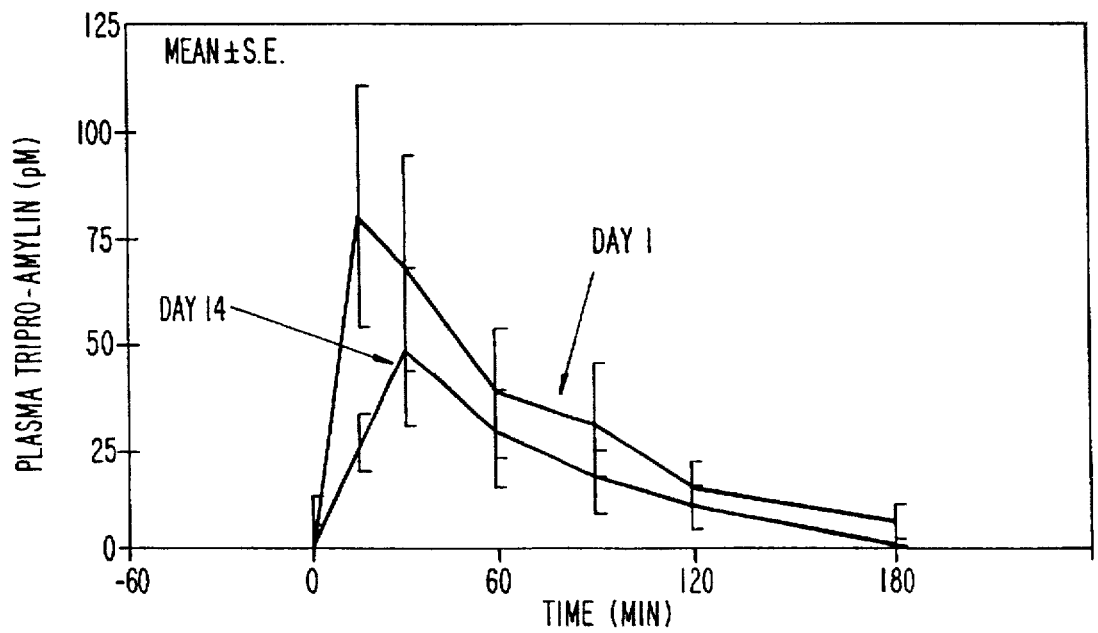
Figure 13A:
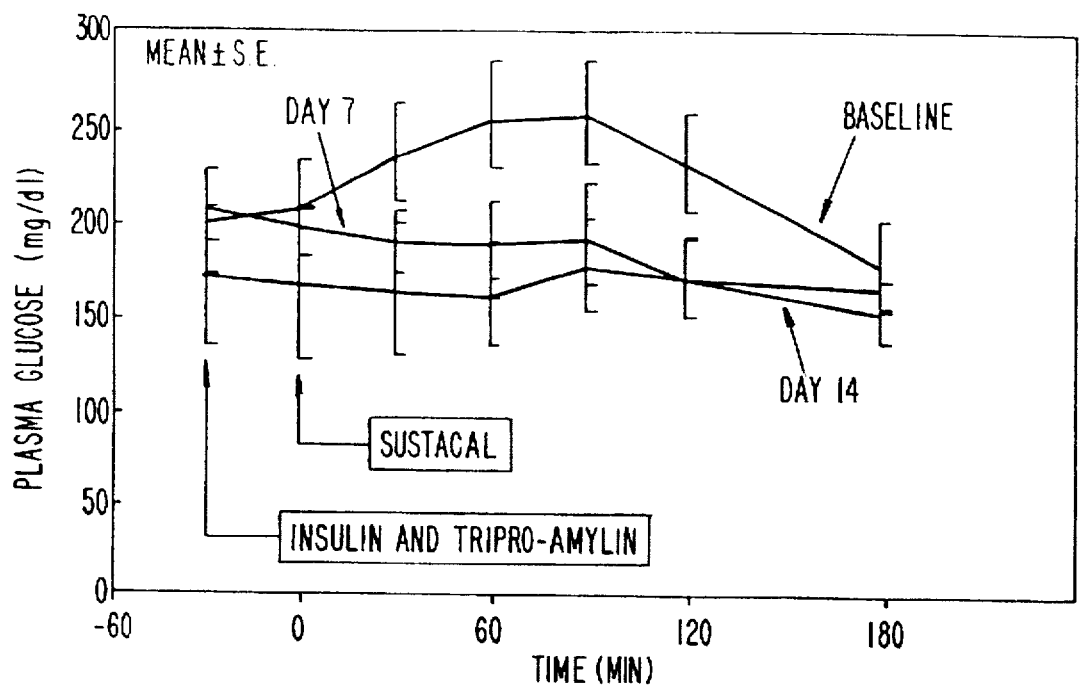
FIGS. 13A and B show the post-Sustacal® meal glucose profiles for baseline (day 1), day 7 and day 14 Sustacal® meal tolerance tests of human clinical volunteers administered 300 µg tripro-amylin (AC-0137) three times a day before meals over a 14-day period.
Figure 13B:
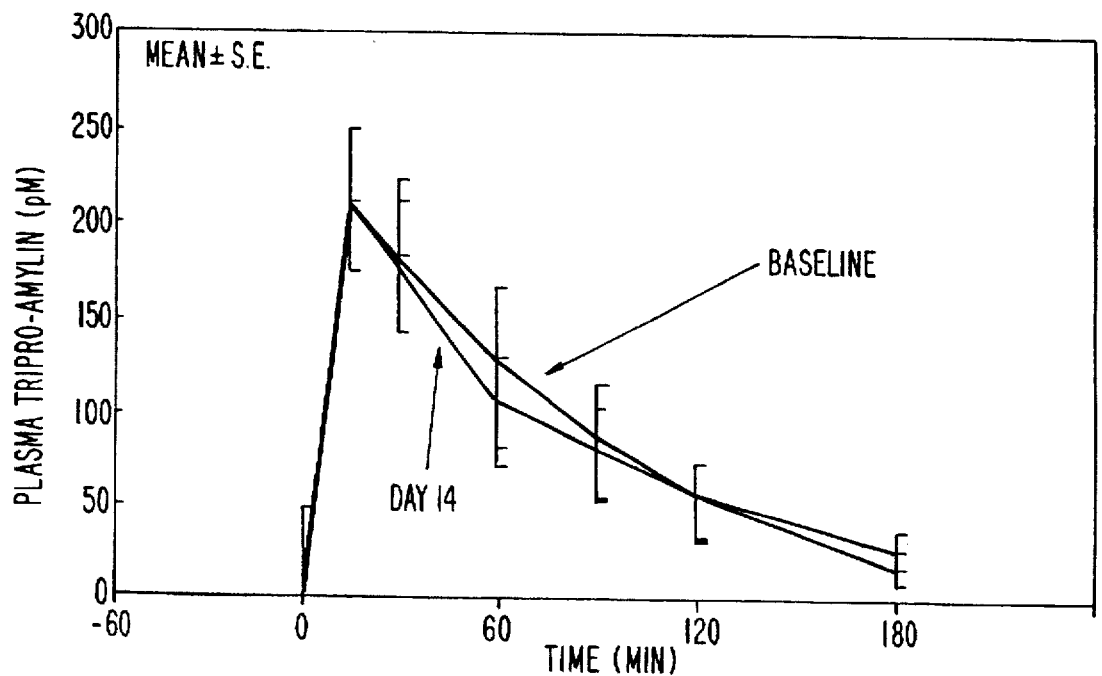

As illustrated in Table 1 below and in FIGS. 11–13, after 14 days, a statistically significant (p=0.02) glucose smoothing effect (measured as area under the glucose curve) was observed at the 30 µg and 100 µg dose levels. The tripro-amylin (AC-0137)—induced reductions in area under the curve (AUC) accompanied average reductions of 45 mg/dl to 60 mg/dl in the peak blood glucose concentrations of the subjects.

TABLE 1

Change in Post Meal Glucose (AUC) After 14 Days of Tripro-amylin

| Tripro-amylin dose (taken 3 times daily) | placebo | 30 micrograms | 100 micrograms | 300 micrograms |
|---|---|---|---|---|
| Number of patients tested at 14 days Post-meal glucose: | 21 | 15 | 22 | 12 |
| Mean of changes in AUC (mg/dl*min.)(a) | +229 | −6,645 | −6,412 | −7,316 |
| "P" values vs. placebo(b) | — | 0.02 | 0.02 | 0.11 |
| Tripro-amylin plasma peaks (picomoles/liter) | — | 22 ± 4 | 44 ± 14 | 173 ± 40 |

(a) AUC is area under the glucose concentration curve relative to pre-meal glucose value, between start of test meal and 3 hours later. Change in AUC is value at pre-dosing minus value at day 14 for each subject tested on both days.
(b) P values obtained from a non-parametric Wilcoxon test.

EXAMPLE 5

The following study was carried out to examine the effects of amylin agonists on gastric emptying in a rodent model of spontaneous autoimmune diabetes, the insulin-treated BB rat.

Male Harlan Sprague Dawley (HSD) rats (161–244 g) and Biobreeding (BB) rats (181–405 g) obtained from an in-house colony originally derived from Mollegard Breeding Center, Denmark in 1989 were used. When BB rats were confirmed as being diabetic by glycosuria on at least 2 days, they were treated with daily s.c. injections of ultralente recombinant human insulin (Humulin-U, Eli Lilly, Ind.). Insulin therapy was aimed at maintaining glucose but minimizing ketones in the urine, in order to avoid hypoglycemic deaths. In fact, glycosuria was present in 88% of measurements and ketonuria in 52%. The average duration of diabetes was 53±5 days, and daily insulin requirements were 4.7±0.3 units. All animals were housed at 22.7±0.8 C in a 12:12 hour light:dark cycle (experiments being performed during the light cycle) and were fed and watered ad libitum (Diet LM-485, Teklad, Madison, Wis.).

The determination of gastric emptying by the method described below has usually been performed after a fast of ~20 hours to ensure that the stomach contained no chyme that would interfere with spectrophotometric absorbance measurements. However, diabetic rats treated with Ultralente insulin could not be fasted for 20 hours. Periods of fasting of greater than 6 hours resulted in hypoglycemia. Such animals were therefore, fasted for only 6 hours before measurement of gastric emptying. Non-diabetic rats were deprived of food for either 6 or 20 hours prior to experimentation. We have noted that even non-diabetic BB rats have elevated glycated hemoglobin concentrations, possibly indicating subclinical insulitis. Both non-diabetic Harlan Sprague Dawley rats and non-diabetic BB rats animals were therefore used in comparisons with diabetic rats. Thus there were 5 treatment groups:

(1) Non-diabetic Harlan Sprague Dawley rats, fasted 6 hours, n=8.

(2) Non-diabetic BB rats, fasted 6 hours, n=6.

(3) Diabetic BB rats, fasted 6 hours, n=10.

(4) Non-diabetic Harlan Sprague Dawley rats, fasted 20 hours, n=20.

(5) Non-diabetic BB rats, fasted 20 hours, n=7.

Conscious rats received by gavage, 1.5 ml of an acaloric gel containing 1.5% methyl cellulose (M-0262, Sigma Chemical Co, St Louis, Mo.) and 0.05% phenol red indicator. Twenty minutes after gavage, rats were anesthetized using 5% halothane, the stomach exposed and clamped at the pyloric and lower esophageal sphincters using artery forceps, removed and opened into an alkaline solution which was made up to a fixed volume. Stomach content was derived from the intensity of the phenol red in the alkaline solution, measured by absorbance at a wavelength of 560 nm. In most experiments, the stomach was clear. In other experiments, particulate gastric contents were centrifuged to clear the solution for absorbance measurements. Where the diluted gastric contents remained turbid, the spectroscopic absorbance due to Phenol Red was derived as the difference between that present in alkaline vs acidified diluent. In separate experiments on 7 rats, the stomach and small intestine were both excised and opened into an alkaline solution. The quantity of phenol red that could be recovered from the upper gastrointestinal tract within 20 minutes of gavage was 89±4%. To account for a maximal dye recovery of less than 100%, stomach contents remaining after 20 min were expressed as a fraction of the gastric contents recovered from control rats sacrificed immediately after gavage in the same experiment.

In baseline studies (where amylin was not injected), gastric emptying over 20 min was determined in the 5 treatment groups described above. In dose-response studies, rat amylin (Bachem, Torrance, Calif.) dissolved in 0.15M saline, was administered as a 0.1 mL subcutaneous bolus in doses of 0, 0.01, 0.1, 1, 10 or 100 µg 5 min before gavage in 46 Harlan-Sprague Dawley (non-diabetic) rats fasted 20 hours (n=17,2,8,8,6,5 respectively) and in 29 diabetic BB rats fasted 6 hours (n=10,-,3,3,3,10 respectively).

In a separate experiment to assess the change in plasma amylin concentrations that an effective dose of subcutaneous amylin produced, blood was sampled from the tails of 6 halothane-anesthetized rats following s.c. bolus injection of either 1 µg (n=3) or 10 µg (n=3) of rat amylin. In another experiment, plasma amylin concentrations were compared in non-fasted Harlan Sprague Dawley rats (n=8) and in non-fasted diabetic BB rats (n=5). The plasma from 250 µL samples collected at 10 min intervals was separated and frozen at −20° C. for analysis by a 2-site immunoenzymometric assay developed in-house.

To perform the immunoassay, black microtiter plates (Dynatech, Chantilly, Va.) were coated with the antibody F024-4.4 [Phelps J L, Blase E, Koda J E, unpublished] by overnight incubation at 4° C. with 20 ug antibody per mL in 50 mM carbonate at pH 9.6. Plates were washed with 0.05M Tris/0.15M sodium chloride/0.02% sodium azide/0.1% Tween 20 (TBS/Tween), and blocked with 1.0% nonfat dry milk powder in the same carbonate buffer for one hour at room temperature. Samples were thawed on ice, and diluted in 4% BSA/200mg/dl bovine cholesterol supertrate (Miles Pentex reagents, Miles Laboratories, Kankakee Ill.) if necessary. Samples or standards were added to the coated and blocked plates and incubated for one hour at room temperature. After washing, the F025-27 detection antibody conjugated to alkaline phosphatase was added. Antibody-enzyme coupling was performed using the maleimide alkaline phosphatase conjugation kit from Pierce Immunochemical Co (Rockford Ill.). The conjugate was incubated for three hours at room temperature, after which plates were washed thoroughly with Tris buffered saline. Bound enzyme was detected by incubation of the plates with the fluorescent substrate 4-methylumbelliferyl phosphate at 50 ug/ml in 1M diethanolamine/0.5 mM MgCl, pH 9.8 for 40 minutes at room temperature. The fluorescent signal was measured with a Dynatech Microfluor plate reader, and data analyzed on Multicalc software (Wallac, Gaithersburg Md.). Concentrations of amylin in plasma samples were determined by comparison with a standard curve run in the same assay. When performed in this manner, the assay has a minimum detectable concentration of 2 pM.

Dose response curves for gastric emptying were fitted to a 4-parameter logistic model using a least-squares iterative routine (ALLFIT, v2.7, NIH, Md.) to derive $ED_{50}$'s. Since $ED_{50}$ is log-normally distributed, it is expressed ± standard error of the logarithm. Pairwise comparisons were performed using one-way analysis of variance and the Student-Newman-Keuls multiple comparisons test (Instat v2.0, GraphPad Software, San Diego) using $P<0.05$ as the level of significance.

In 8 non-fasted Harlan Sprague Dawley rats, circulating amylin concentrations were 11.7±1.4 pM (95% CI 8.4–14.9 pM). By comparison, amylin concentrations in 5 non-fasted spontaneously diabetic BB rats were undetectable.

The fractions of dye remaining 20 minutes after gavage with Phenol Red, together with relevant statistical comparisons, are shown in Table 2. In both Harlan Sprague Dawley rats and in non-diabetic BB rats, emptying of dye after 20 minutes was the same whether animals were fasted for 6 hours or for 20 hours. That is, period of fasting (within the 6–20 hour range) did not appear to significantly affect gastric emptying measured by this technique.

TABLE 2

| | Gastric contents remaining 20 minutes after gavage | | |
|---|---|---|---|
| | Non-diabetic HSD | Non-diabetic BB | Diabetic BB |
| Fasted 20 hr | 54.9 ± 3.0% n = 20 | 27.0 ± 3.8% n = 7 | not done |
| Fasted 6 hr | 50.9 ± 4.7% n = 8[a] | 38.9 ± 9.2% n = 6[a] | 9.7 ± 1.7% n = 10[b,c] |

Gastric contents are expressed as a fraction of those that could be recovered immediately after gavage in 2–3 separate rats run in the same assay.
[a]= not different from rats fasted 20 hours
[b]= different from HSD rats fasted 6 hours (P < 0.001)
[c]= different from non-diabetic BB rats fasted 6 hours (P < 0.001)

It is worth noting that gastric emptying in diabetic BB rats was significantly faster (P<0.01–0.001) than any of the 4 other treatment groups (ie. non-diabetic animals). The observation that diabetic BB rats have a higher rate of gastric emptying than non-diabetic BB rats suggests that the observation is related to the presence of diabetes and is not merely associated with the BB strain.

Figure 14:
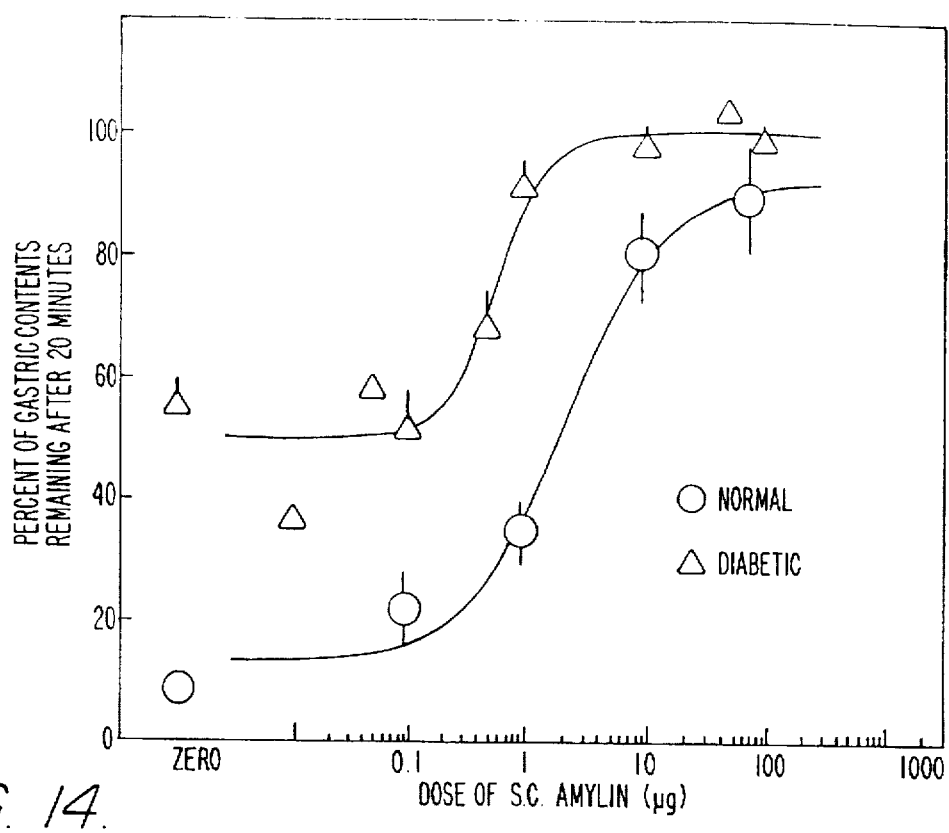
FIG. 14 shows dose-response effects of prior subcutaneous injection of rat amylin on the retention of gastric contents 20 minutes after gavage in normal and diabetic BB rats (n=3–9 for each point). Symbols are means ± SEM and the curves define the best fitting logistic functions. "Zero"

Because of the methodological constraints identified above, the effects of amylin were explored in non-diabetic Harlan Sprague-Dawley rats fasted 20 hours, and in diabetic BB rats fasted 6 hours. When subcutaneous amylin injections were given 5 min before gavage with Phenol Red indicator, there was a dose dependent suppression of gastric emptying. Suppression of gastric emptying was such that the dye recoverable from normal HSD rats administered 1 µg of amylin, and diabetic rats administered 1 µg, was the same as that recoverable immediately after gavage (P=0.22, 0.14). The dose at which 50% of the maximal change in gastric emptying ($ED_{50}$) was observed in normal rats was 0.43 µg (0.60 nmole amylin/kg body weight)±0.19 log units. In diabetic rats the $ED_{50}$ for suppression of gastric emptying was 2.2 µg (2.3 nmol/kg)±0.18 log units. From the fitted curves shown in FIG. 14, it can be estimated that a dose of amylin of ~2 µg administered to a diabetic rat would restore gastric emptying to the rate observed in normal rats not administered amylin.

As shown in FIG. 15, when 3 rats were injected subcutaneously with 1 µg of rat amylin, the plasma concentration measured 10 min later was 66±10 pM and the peak concentration, at 20 min, was 74±26 pM. In 3 rats injected with a 10 µg s.c. bolus, the corresponding 10 and 20 min concentrations were 347±43 pM and 301±57 pM, respectively. A 1 µg subcutaneous amylin dose, which inhibits gastric emptying by ~50% over 20 minutes (the $ED_{50}$), must begin working soon after injection to have an effect 20 min later. An effect that began around 20 min after injection, for example, would not be detected in this system. It follows that plasma concentrations 50% effective in inhibiting gastric emptying (the $EC_{50}$) occurred well before peak plasma concentrations of 74 pM were reached, and therefore were considerably less than 74 pM.

The results of these experiments show that amylin potently and dose-dependently inhibits gastric emptying.

EXAMPLE 6

The experiments described in this example were carried out to examine the effects of an amylin receptor antagonist on oral glucose tolerance and the absorption of tritium derived from a labelled oral glucose load.

Uptake of an ingested labelled glucose load was measured in 11 conscious 24-hr fasted corpulent (500–600 g) LA/N rats on 2 occasions, 14 days apart. On one occasion, rats were injected subcutaneously with 3 µg of the selective amylin antagonist AC-0187 (acetyl-$^{10}$Asn$^{32}$Tyr$^{8-32}$salmon calcitonin [SEQ. ID. NO.30], 3 minutes before gavage. On the other occasion, rats were preinjected with saline vehicle alone. Rats were gavaged with 5 µCi of [$3^3$H]glucose in 1 ml of 50% glucose. Blood samples were taken from anesthetized tails 0, 15, 30, 60, 90 and 120 minutes after gavage were assayed for glucose-derived tritium and glucose.

Preinjection with the amylin antagonist, AC-0187, accelerated the appearance of glucose-derived tritium in the plasma by 48% after 15 minutes post-gavage (P<0.02), and by 45% (P<0.001) after 30 minutes post-gavage (paired t-test). Preinjection with AC-0187 also resulted in a greater rise in plasma glucose 15 minutes after gavage with 0.5 g glucose (5.89±0.17 to 8.33±0.28 mM vs. 5.83±0.22 to 6.83±0.28 mM, P<0.001, paired t-test). Additionally, in AC-0187-treated animals, plasma glucose declined earlier (6.89±0.28 mM vs. 8.17±0.39 mM after gavage 60 minutes after glucose gavage, P<0.001, paired t-test).

Thus, in the LA/N corpulent rat, a selective amylin antagonist increased the rate of appearance in plasma of labelled glucose after an oral glucose load, and also increased the rate of rise and fall in the plasma concentration of unlabelled glucose. These data are consistent with the amylin antagonist having counteracted an effect of endogenously secreted amylin, thereby accelerating gastric emptying.

We claim:

1. A method of treating gastric hypomotility in a subject comprising administering to said subject a therapeutically effective amount of an amylin antagonist.

2. A method of accelerating gastric emptying in a subject comprising administering to said subject a therapeutically effective amount of an amylin antagonist.

3. The method of claim 1 or 2 wherein said hypomotility is a consequence of diabetic neuropathy.

4. The method of claim 1 or 2 wherein said hypomotility is a consequence of anorexia nervosa.

5. A method according to any of claims 1–4 wherein said amylin antagonist is an amylin receptor antagonist.

6. A method according to claim 5 wherein said amylin antagonist is acetyl-$^{11,18}$Arg, $^{30}$Asn, $^{32}$Tyr-$^{9-32}$calcitonin (salmon) [SEQ. ID. NO.3].

* * * * *